(12) United States Patent
Olivera et al.

(10) Patent No.: US 9,731,148 B2
(45) Date of Patent: Aug. 15, 2017

(54) RADIATION THERAPY IMAGING AND DELIVERY UTILIZING COORDINATED MOTION OF GANTRY AND COUCH

(75) Inventors: Gustavo H. Olivera, Madison, WI (US); Thomas R. Mackie, Verona, WI (US); Kenneth J. Ruchala, Madison, WI (US); Paul J. Reckwerdt, Madison, WI (US); John H. Hughes, Madison, WI (US); Jeffrey M. Kapatoes, Madison, WI (US); Eric Schnarr, McFarland, WI (US); Weiguo Lu, Madison, WI (US); Eric Schloesser, Mount Horeb, WI (US); Gerald D. Fordyce, II, Madison, WI (US); Tim Holzmann, Verona, WI (US)

(73) Assignee: TOMOTHERAPY INCORPORATED, Madison, WI (US)

( * ) Notice: Subject to any disclaimer, the term of this patent is extended or adjusted under 35 U.S.C. 154(b) by 1405 days.

(21) Appl. No.: 11/459,161

(22) Filed: Jul. 21, 2006

(65) Prior Publication Data
US 2007/0041500 A1    Feb. 22, 2007

Related U.S. Application Data

(60) Provisional application No. 60/701,585, filed on Jul. 23, 2005.

(51) Int. Cl.
*A61B 5/00* (2006.01)
*A61N 5/10* (2006.01)

(52) U.S. Cl.
CPC .......... *A61N 5/1042* (2013.01); *A61N 5/1049* (2013.01); *A61N 5/1069* (2013.01)

(58) Field of Classification Search
CPC ...... A61B 6/032; A61B 6/027; A61N 5/1069; A61N 5/107; A61N 5/1049; A61N 2005/1061
(Continued)

(56) References Cited

U.S. PATENT DOCUMENTS 2,781,454 A * 2/1957 Green et al. .................... 378/65
2,793,296 A * 5/1957 Peterson, Jr. ................... 378/65
(Continued)

FOREIGN PATENT DOCUMENTS

CA    2091275    9/1993
CA    2180227    12/1996
(Continued)

OTHER PUBLICATIONS

JS Welsh, RR Patel, MA Ritter, PM Harari, TR Mackie, MP Mehta. Helical tomotherapy: an innovative technology and approach to radiation therapy. Technology in Cancer Research and Treatment. Aug. 2002: pp. 311-316.*

(Continued)

*Primary Examiner* — Amanda Lauritzen Moher
(74) *Attorney, Agent, or Firm* — Michael Best & Friedrich LLP

(57) ABSTRACT

A system and method of delivering a radiation therapy treatment plan to a patient. The treatment plan is delivered using a radiation therapy system including a moveable support for supporting a patient, a gantry moveable relative to the support and supporting a radiation source and multi-leaf collimator for modulating the radiation source. The support and gantry are moved during delivery of the treatment plan.

35 Claims, 10 Drawing Sheets

(58) Field of Classification Search
USPC .............. 600/425, 427, 428; 378/17, 68, 69;
250/492.3, 505.1, 526; 5/600, 601
See application file for complete search history.

(56) References Cited

U.S. PATENT DOCUMENTS

| | | |
|---|---|---|
| 3,949,265 A | 4/1976 | Holl |
| 3,964,467 A | 6/1976 | Rose |
| 4,006,422 A | 2/1977 | Schriber |
| 4,032,810 A | 6/1977 | Eastham et al. |
| 4,149,081 A | 4/1979 | Seppi |
| 4,181,894 A | 1/1980 | Pottier |
| 4,189,470 A | 2/1980 | Rose |
| 4,208,185 A | 6/1980 | Sawai et al. |
| 4,273,867 A | 6/1981 | Lin et al. |
| 4,314,180 A | 2/1982 | Salisbury |
| 4,335,465 A | 6/1982 | Christiansen et al. |
| 4,388,560 A | 6/1983 | Robinson et al. |
| 4,393,334 A | 7/1983 | Glaser |
| 4,395,631 A | 7/1983 | Salisbury |
| 4,401,765 A | 8/1983 | Craig et al. |
| 4,426,582 A | 1/1984 | Orloff et al. |
| 4,446,403 A | 5/1984 | Cuomo et al. |
| 4,480,042 A | 10/1984 | Craig et al. |
| 4,570,103 A | 2/1986 | Schoen |
| 4,664,869 A | 5/1987 | Mirzadeh et al. |
| 4,703,018 A | 10/1987 | Craig et al. |
| 4,715,056 A | 12/1987 | Vlasbloem et al. |
| 4,736,106 A | 4/1988 | Kashy et al. |
| 4,752,692 A | 6/1988 | Jergenson et al. |
| 4,754,760 A | 7/1988 | Fukukita et al. |
| 4,815,446 A | 3/1989 | McIntosh |
| 4,818,914 A | 4/1989 | Brodie |
| 4,868,843 A * | 9/1989 | Nunan ........................ 378/152 |
| 4,868,844 A | 9/1989 | Nunan |
| 4,870,287 A | 9/1989 | Cole et al. |
| 4,879,518 A | 11/1989 | Broadhurst |
| 4,912,731 A | 3/1990 | Nardi |
| 4,936,308 A | 6/1990 | Fukukita et al. |
| 4,987,309 A | 1/1991 | Klasen et al. |
| 4,998,268 A | 3/1991 | Winter |
| 5,003,998 A | 4/1991 | Collett |
| 5,008,907 A | 4/1991 | Norman et al. |
| 5,012,111 A | 4/1991 | Ueda |
| 5,044,354 A | 9/1991 | Goldhorn et al. |
| 5,065,315 A | 11/1991 | Garcia |
| 5,073,913 A | 12/1991 | Martin |
| 5,084,682 A | 1/1992 | Swenson et al. |
| 5,107,222 A | 4/1992 | Tsuzuki |
| 5,117,829 A | 6/1992 | Miller et al. |
| 5,124,658 A | 6/1992 | Adler |
| 5,138,647 A | 8/1992 | Nguyen et al. |
| 5,210,414 A | 5/1993 | Wallace et al. |
| 5,250,388 A | 10/1993 | Schoch, Jr. et al. |
| 5,317,616 A | 5/1994 | Swerdloff et al. |
| 5,332,908 A | 7/1994 | Weidlich |
| 5,335,255 A | 8/1994 | Seppi et al. |
| 5,346,548 A | 9/1994 | Mehta |
| 5,351,280 A | 9/1994 | Swerdloff et al. |
| 5,382,914 A | 1/1995 | Hamm et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A * | 8/1995 | Swerdloff et al. .............. 378/65 |
| 5,446,548 A | 8/1995 | Gerig et al. |
| 5,453,310 A | 9/1995 | Andersen et al. |
| 5,466,587 A | 11/1995 | Fitzpatrick-McElligott et al. |
| 5,471,516 A | 11/1995 | Nunan |
| 5,483,122 A | 1/1996 | Derbenev et al. |
| 5,489,780 A | 2/1996 | Diamondis |
| 5,511,549 A | 4/1996 | Legg et al. |
| 5,523,578 A | 6/1996 | Herskovic |
| 5,528,650 A | 6/1996 | Swerdloff et al. |
| 5,548,627 A * | 8/1996 | Swerdloff et al. ................ 378/4 |
| 5,552,605 A | 9/1996 | Arata |
| 5,576,602 A | 11/1996 | Hiramoto et al. |
| 5,578,909 A | 11/1996 | Billen |
| 5,579,358 A | 11/1996 | Lin |
| 5,581,156 A | 12/1996 | Roberts et al. |
| 5,596,619 A | 1/1997 | Carol |
| 5,596,653 A | 1/1997 | Kurokawa |
| 5,621,779 A | 4/1997 | Hughes et al. |
| 5,622,187 A | 4/1997 | Carol |
| 5,625,663 A | 4/1997 | Swerdloff et al. |
| 5,627,041 A | 5/1997 | Shartle |
| 5,641,584 A | 6/1997 | Andersen et al. |
| 5,647,663 A | 7/1997 | Holmes |
| 5,651,043 A | 7/1997 | Tsuyuki et al. |
| 5,661,377 A | 8/1997 | Mishin et al. |
| 5,661,773 A | 8/1997 | Swerdloff et al. |
| 5,667,803 A | 9/1997 | Paronen et al. |
| 5,668,371 A | 9/1997 | Deasy et al. |
| 5,673,300 A | 9/1997 | Reckwerdt et al. |
| 5,692,507 A | 12/1997 | Seppi et al. |
| 5,695,443 A | 12/1997 | Brent et al. |
| 5,712,482 A | 1/1998 | Gaiser et al. |
| 5,721,123 A | 2/1998 | Hayes et al. |
| 5,724,400 A | 3/1998 | Swerdloff et al. |
| 5,729,028 A | 3/1998 | Rose |
| 5,734,168 A | 3/1998 | Yao |
| 5,747,254 A | 5/1998 | Pontius |
| 5,751,781 A | 5/1998 | Brown et al. |
| 5,753,308 A | 5/1998 | Andersen et al. |
| 5,754,622 A | 5/1998 | Hughes |
| 5,754,623 A | 5/1998 | Seki |
| 5,760,395 A | 6/1998 | Johnstone |
| 5,802,136 A | 9/1998 | Carol |
| 5,810,707 A * | 9/1998 | Montebello et al. .............. 600/1 |
| 5,811,944 A | 9/1998 | Sampayan et al. |
| 5,815,547 A | 9/1998 | Shepherd et al. |
| 5,818,058 A | 10/1998 | Nakanishi et al. |
| 5,818,902 A | 10/1998 | Yu |
| 5,820,553 A | 10/1998 | Hughes |
| 5,821,051 A | 10/1998 | Androphy et al. |
| 5,821,705 A | 10/1998 | Caporaso et al. |
| 5,823,192 A | 10/1998 | Kalend et al. |
| 5,834,454 A | 11/1998 | Kitano et al. |
| 5,835,562 A | 11/1998 | Ramsdell et al. |
| 5,836,905 A | 11/1998 | Lemelson et al. |
| 5,838,765 A | 11/1998 | Gershman et al. |
| 5,842,175 A | 11/1998 | Andros et al. |
| 5,866,912 A | 2/1999 | Slater et al. |
| 5,870,447 A | 2/1999 | Powell et al. |
| 5,877,023 A | 3/1999 | Sautter et al. |
| 5,877,192 A | 3/1999 | Lindberg et al. |
| 5,912,134 A | 6/1999 | Shartle |
| 5,920,601 A | 7/1999 | Nigg et al. |
| 5,953,461 A | 9/1999 | Yamada |
| 5,962,995 A | 10/1999 | Avnery |
| 5,963,615 A | 10/1999 | Egley et al. |
| 5,969,367 A | 10/1999 | Hiramoto et al. |
| 5,977,100 A | 11/1999 | Kitano et al. |
| 5,983,424 A | 11/1999 | Naslund |
| 5,986,274 A | 11/1999 | Akiyama et al. |
| 6,011,825 A | 1/2000 | Welch et al. |
| 6,020,135 A | 2/2000 | Levine et al. |
| 6,020,538 A | 2/2000 | Han et al. |
| 6,029,079 A | 2/2000 | Cox et al. |
| 6,038,283 A | 3/2000 | Carol et al. |
| 6,045,262 A | 4/2000 | Igeta et al. |
| 6,049,587 A | 4/2000 | Leksell et al. |
| 6,066,927 A | 5/2000 | Koudijs |
| 6,069,459 A | 5/2000 | Koudijs |
| 6,071,748 A | 6/2000 | Modlin et al. |
| 6,094,760 A | 8/2000 | Nonaka et al. |
| 6,127,688 A | 10/2000 | Wu |
| 6,152,599 A | 11/2000 | Salter |
| 6,171,798 B1 | 1/2001 | Levine et al. |
| 6,178,345 B1 | 1/2001 | Vilsmeier et al. |
| 6,197,328 B1 | 3/2001 | Yanagawa |
| 6,198,957 B1 | 3/2001 | Green |
| 6,200,959 B1 | 3/2001 | Haynes et al. |
| 6,204,510 B1 | 3/2001 | Ohkawa |
| 6,207,400 B1 | 3/2001 | Kwon |

(56) References Cited

U.S. PATENT DOCUMENTS

| | | | |
|---|---|---|---|
| 6,218,675 B1 | 4/2001 | Akiyama et al. | |
| 6,222,905 B1 | 4/2001 | Yoda et al. | |
| 6,241,670 B1 | 6/2001 | Nambu | |
| 6,242,747 B1 | 6/2001 | Sugitani et al. | |
| 6,260,005 B1 | 7/2001 | Yang et al. | |
| 6,264,825 B1 | 7/2001 | Blackburn et al. | |
| 6,265,837 B1 | 7/2001 | Akiyama et al. | |
| 6,279,579 B1 | 8/2001 | Riaziat et al. | |
| 6,291,823 B1 | 9/2001 | Doyle et al. | |
| 6,316,776 B1 | 11/2001 | Hiramoto et al. | |
| 6,319,469 B1 | 11/2001 | Mian et al. | |
| 6,322,249 B1 | 11/2001 | Wofford et al. | |
| 6,331,194 B1 | 12/2001 | Elizondo-Decanini et al. | |
| 6,345,114 B1 | 2/2002 | Mackie et al. | |
| 6,360,116 B1 | 3/2002 | Jackson, Jr. et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,405,072 B1 | 6/2002 | Cosman | |
| 6,407,505 B1 | 6/2002 | Bertsche | |
| 6,417,178 B1 | 7/2002 | Klunk et al. | |
| 6,422,748 B1 * | 7/2002 | Shepherd et al. | 378/203 |
| 6,424,856 B1 | 7/2002 | Vilsmeier et al. | |
| 6,428,547 B1 | 8/2002 | Vilsmeier et al. | |
| 6,433,349 B2 | 8/2002 | Akiyama et al. | |
| 6,438,202 B1 | 8/2002 | Olivera et al. | |
| 6,455,844 B1 | 9/2002 | Meyer | |
| 6,459,769 B1 | 10/2002 | Cosman | |
| 6,462,490 B1 | 10/2002 | Matsuda et al. | |
| 6,465,957 B1 | 10/2002 | Whitham et al. | |
| 6,466,644 B1 | 10/2002 | Hughes et al. | |
| 6,469,058 B1 | 10/2002 | Grove et al. | |
| 6,472,834 B2 | 10/2002 | Hiramoto et al. | |
| 6,473,490 B1 | 10/2002 | Siochi | |
| 6,475,994 B2 | 11/2002 | Tomalia et al. | |
| 6,482,604 B2 | 11/2002 | Kwon | |
| 6,484,144 B2 | 11/2002 | Martin et al. | |
| 6,487,274 B2 | 11/2002 | Bertsche | |
| 6,493,424 B2 | 12/2002 | Whitham | |
| 6,497,358 B1 | 12/2002 | Walsh | |
| 6,498,011 B2 | 12/2002 | Hohn et al. | |
| 6,500,343 B2 | 12/2002 | Siddiqi | |
| 6,504,899 B2 | 1/2003 | Pugachev et al. | |
| 6,510,199 B1 | 1/2003 | Hughes et al. | |
| 6,512,942 B1 | 1/2003 | Burdette et al. | |
| 6,516,046 B1 | 2/2003 | Frohlich et al. | |
| 6,527,443 B1 | 3/2003 | Vilsmeier et al. | |
| 6,531,449 B2 | 3/2003 | Khojasteh et al. | |
| 6,535,837 B1 | 3/2003 | Schach Von Wittenau | |
| 6,539,247 B2 | 3/2003 | Spetz | |
| 6,552,338 B1 | 4/2003 | Doyle | |
| 6,558,961 B1 | 5/2003 | Sarphie et al. | |
| 6,560,311 B1 | 5/2003 | Shepard et al. | |
| 6,562,376 B2 | 5/2003 | Hooper et al. | |
| 6,584,174 B2 | 6/2003 | Schubert et al. | |
| 6,586,409 B1 | 7/2003 | Wheeler | |
| 6,605,297 B2 | 8/2003 | Nadachi et al. | |
| 6,611,700 B1 | 8/2003 | Vilsmeier et al. | |
| 6,617,768 B1 | 9/2003 | Hansen | |
| 6,618,467 B1 | 9/2003 | Ruchala et al. | |
| 6,621,889 B1 | 9/2003 | Mostafavi | |
| 6,633,686 B1 | 10/2003 | Bakircioglu et al. | |
| 6,634,790 B1 | 10/2003 | Salter, Jr. | |
| 6,636,622 B2 | 10/2003 | Mackie et al. | |
| 6,637,056 B1 | 10/2003 | Tybinkowski et al. | |
| 6,646,383 B2 | 11/2003 | Bertsche et al. | |
| 6,653,547 B2 | 11/2003 | Akamatsu | |
| 6,661,870 B2 | 12/2003 | Kapatoes et al. | |
| 6,688,187 B2 | 2/2004 | Masquelier | |
| 6,690,965 B1 | 2/2004 | Riaziat et al. | |
| 6,697,452 B2 | 2/2004 | Xing | |
| 6,705,984 B1 | 3/2004 | Angha | |
| 6,713,668 B2 | 3/2004 | Akamatsu | |
| 6,713,976 B1 | 3/2004 | Zumoto et al. | |
| 6,714,620 B2 | 3/2004 | Caflisch et al. | |
| 6,714,629 B2 | 3/2004 | Vilsmeier | |
| 6,716,162 B2 | 4/2004 | Hakamata | |
| 6,723,334 B1 | 4/2004 | McGee et al. | |
| 6,735,277 B2 * | 5/2004 | McNutt et al. | 378/65 |
| 6,757,355 B1 | 6/2004 | Siochi | |
| 6,760,402 B2 | 7/2004 | Ghelmansarai | |
| 6,774,383 B2 | 8/2004 | Norimine et al. | |
| 6,787,771 B2 | 9/2004 | Bashkirov et al. | |
| 6,787,983 B2 | 9/2004 | Yamanobe et al. | |
| 6,788,764 B2 | 9/2004 | Saladin et al. | |
| 6,792,073 B2 | 9/2004 | Deasy et al. | |
| 6,796,164 B2 | 9/2004 | McLoughlin et al. | |
| 6,800,866 B2 | 10/2004 | Amemiya et al. | |
| 6,822,244 B2 | 11/2004 | Beloussov et al. | |
| 6,822,247 B2 | 11/2004 | Sasaki | |
| 6,838,676 B1 | 1/2005 | Jackson | |
| 6,842,502 B2 | 1/2005 | Jaffray et al. | |
| 6,844,689 B1 | 1/2005 | Brown et al. | |
| 6,865,254 B2 | 3/2005 | Nafstadius | |
| 6,871,171 B1 | 3/2005 | Agur et al. | |
| 6,873,115 B2 | 3/2005 | Sagawa et al. | |
| 6,873,123 B2 | 3/2005 | Marchand et al. | |
| 6,878,951 B2 * | 4/2005 | Ma | 250/505.1 |
| 6,882,702 B2 | 4/2005 | Luo | |
| 6,882,705 B2 | 4/2005 | Egley et al. | |
| 6,888,326 B2 | 5/2005 | Amaldi et al. | |
| 6,889,695 B2 | 5/2005 | Pankratov et al. | |
| 6,922,455 B2 | 7/2005 | Jurczyk et al. | |
| 6,929,398 B1 | 8/2005 | Tybinkowski et al. | |
| 6,936,832 B2 | 8/2005 | Norimine et al. | |
| 6,955,464 B1 | 10/2005 | Tybinkowski et al. | |
| 6,961,405 B2 | 11/2005 | Scherch | |
| 6,963,171 B2 | 11/2005 | Sagawa et al. | |
| 6,974,254 B2 | 12/2005 | Paliwal et al. | |
| 6,977,984 B2 * | 12/2005 | Hsieh et al. | 378/4 |
| 6,984,835 B2 | 1/2006 | Harada | |
| 6,990,167 B2 | 1/2006 | Chen | |
| 7,015,490 B2 | 3/2006 | Wang et al. | |
| 7,046,762 B2 | 5/2006 | Lee | |
| 7,051,605 B2 | 5/2006 | Lagraff et al. | |
| 7,054,413 B2 | 5/2006 | Steinberg | |
| 7,060,997 B2 | 6/2006 | Norimine et al. | |
| 7,077,569 B1 | 7/2006 | Tybinkowski et al. | |
| 7,081,619 B2 | 7/2006 | Bashkirov et al. | |
| 7,084,410 B2 | 8/2006 | Beloussov et al. | |
| 7,087,200 B2 | 8/2006 | Taboas et al. | |
| 7,112,924 B2 | 9/2006 | Hanna | |
| 7,130,372 B2 | 10/2006 | Kusch et al. | |
| 7,154,991 B2 | 12/2006 | Earnst et al. | |
| 7,177,386 B2 | 2/2007 | Mostafavi et al. | |
| 7,186,986 B2 | 3/2007 | Hinderer et al. | |
| 7,186,991 B2 | 3/2007 | Kato et al. | |
| 7,187,752 B2 | 3/2007 | Kotler et al. | |
| 7,203,272 B2 | 4/2007 | Chen | |
| 7,209,547 B2 | 4/2007 | Baier et al. | |
| 7,221,729 B2 * | 5/2007 | Wakai et al. | 378/8 |
| 7,221,733 B1 | 5/2007 | Takai et al. | |
| 7,252,307 B2 | 8/2007 | Kanbe et al. | |
| 7,257,196 B2 | 8/2007 | Brown et al. | |
| 7,265,356 B2 | 9/2007 | Pelizzari et al. | |
| 7,295,648 B2 * | 11/2007 | Brown | 378/65 |
| 7,382,858 B2 * | 6/2008 | Gohno | 378/98.12 |
| 7,450,687 B2 | 11/2008 | Yeo et al. | |
| 7,469,035 B2 | 12/2008 | Keall et al. | |
| 7,477,721 B2 | 1/2009 | Chappo et al. | |
| 7,492,858 B2 * | 2/2009 | Partain et al. | 378/37 |
| 7,519,150 B2 | 4/2009 | Romesberg et al. | |
| 7,551,717 B2 | 6/2009 | Tome et al. | |
| 7,613,501 B2 * | 11/2009 | Scherch | 600/427 |
| 7,629,599 B2 * | 12/2009 | Hashimoto | 250/505.1 |
| 7,640,607 B2 * | 1/2010 | Guertin et al. | 5/601 |
| 7,708,682 B2 | 5/2010 | Pekar et al. | |
| 7,831,289 B2 | 11/2010 | Riker et al. | |
| 7,881,431 B2 | 2/2011 | Aoi et al. | |
| 7,940,891 B2 | 5/2011 | Star-lack et al. | |
| 7,974,681 B2 | 7/2011 | Wallace et al. | |
| 7,983,380 B2 | 7/2011 | Guertin et al. | |
| 8,073,104 B2 | 12/2011 | Yan et al. | |
| 8,085,899 B2 | 12/2011 | Nord et al. | |

(56) References Cited

U.S. PATENT DOCUMENTS

| | | | |
|---|---|---|---|
| 8,175,892 B2* | 5/2012 | Kapoor et al. | 705/2 |
| 8,331,532 B2* | 12/2012 | Nord et al. | 378/65 |
| 8,509,383 B2* | 8/2013 | Lu et al. | 378/65 |
| 2002/0007918 A1 | 1/2002 | Owen et al. | |
| 2002/0077545 A1 | 6/2002 | Takahashi et al. | |
| 2002/0080915 A1 | 6/2002 | Frohlich | |
| 2002/0085668 A1 | 7/2002 | Blumhofer et al. | |
| 2002/0091314 A1 | 7/2002 | Schlossbauer et al. | |
| 2002/0115923 A1 | 8/2002 | Erbel | |
| 2002/0120986 A1* | 9/2002 | Erbel | A61B 6/0421 5/601 |
| 2002/0122530 A1 | 9/2002 | Erbel et al. | |
| 2002/0136439 A1 | 9/2002 | Ruchala et al. | |
| 2002/0150207 A1 | 10/2002 | Kapatoes et al. | |
| 2002/0187502 A1 | 12/2002 | Waterman et al. | |
| 2002/0193685 A1 | 12/2002 | Mate et al. | |
| 2003/0007601 A1 | 1/2003 | Jaffray et al. | |
| 2003/0031298 A1 | 2/2003 | Xing | |
| 2003/0048868 A1* | 3/2003 | Bailey et al. | 378/65 |
| 2003/0086527 A1 | 5/2003 | Speiser et al. | |
| 2003/0105650 A1 | 6/2003 | Lombardo et al. | |
| 2003/0174872 A1 | 9/2003 | Chalana et al. | |
| 2003/0176779 A1* | 9/2003 | Ghelmansarai | 600/407 |
| 2004/0010418 A1 | 1/2004 | Buonocore et al. | |
| 2004/0024300 A1 | 2/2004 | Graf | |
| 2004/0068182 A1 | 4/2004 | Misra | |
| 2004/0096033 A1 | 5/2004 | Seppi et al. | |
| 2004/0116804 A1 | 6/2004 | Mostafavi | |
| 2004/0120452 A1 | 6/2004 | Shapiro et al. | |
| 2004/0165696 A1 | 8/2004 | Lee | |
| 2004/0184578 A1* | 9/2004 | Nakano | 378/65 |
| 2004/0202280 A1 | 10/2004 | Besson | |
| 2004/0202610 A1* | 10/2004 | Adair | 424/1.11 |
| 2004/0230115 A1 | 11/2004 | Scarantino et al. | |
| 2004/0254492 A1 | 12/2004 | Zhang et al. | |
| 2004/0254773 A1 | 12/2004 | Zhang et al. | |
| 2004/0264640 A1 | 12/2004 | Myles | |
| 2005/0013406 A1 | 1/2005 | Dyk et al. | |
| 2005/0031181 A1 | 2/2005 | Bi et al. | |
| 2005/0080332 A1 | 4/2005 | Shiu et al. | |
| 2005/0089141 A1* | 4/2005 | Brown | 378/65 |
| 2005/0096515 A1 | 5/2005 | Geng | |
| 2005/0123092 A1 | 6/2005 | Mistretta et al. | |
| 2005/0143965 A1 | 6/2005 | Failla et al. | |
| 2005/0180544 A1 | 8/2005 | Sauer et al. | |
| 2005/0197564 A1 | 9/2005 | Dempsey | |
| 2005/0201515 A1 | 9/2005 | Mitschke | |
| 2005/0201516 A1* | 9/2005 | Ruchala et al. | 378/65 |
| 2005/0251029 A1 | 11/2005 | Khamene et al. | |
| 2006/0072699 A1* | 4/2006 | Mackie et al. | 378/4 |
| 2006/0074292 A1 | 4/2006 | Thomson et al. | |
| 2006/0083349 A1 | 4/2006 | Harari et al. | |
| 2006/0100738 A1 | 5/2006 | Alsafadi et al. | |
| 2006/0133568 A1 | 6/2006 | Moore | |
| 2006/0153330 A1 | 7/2006 | Wong et al. | |
| 2006/0173294 A1* | 8/2006 | Ein-Gal | 600/427 |
| 2006/0193429 A1 | 8/2006 | Chen | |
| 2006/0193441 A1 | 8/2006 | Cadman | |
| 2006/0241332 A1 | 10/2006 | Klein et al. | |
| 2006/0285639 A1 | 12/2006 | Olivera et al. | |
| 2006/0285640 A1 | 12/2006 | Nizin et al. | |
| 2007/0041494 A1 | 2/2007 | Ruchala et al. | |
| 2007/0041495 A1 | 2/2007 | Olivera et al. | |
| 2007/0041496 A1 | 2/2007 | Olivera et al. | |
| 2007/0041497 A1 | 2/2007 | Schnarr et al. | |
| 2007/0041498 A1 | 2/2007 | Olivera et al. | |
| 2007/0041499 A1 | 2/2007 | Lu et al. | |
| 2007/0041500 A1 | 2/2007 | Olivera et al. | |
| 2007/0043286 A1 | 2/2007 | Lu et al. | |
| 2007/0076846 A1 | 4/2007 | Ruchala et al. | |
| 2007/0088573 A1 | 4/2007 | Ruchala et al. | |
| 2007/0104316 A1 | 5/2007 | Ruchala et al. | |
| 2007/0127623 A1 | 6/2007 | Goldman et al. | |
| 2007/0127790 A1 | 6/2007 | Lau et al. | |
| 2007/0189591 A1 | 8/2007 | Lu et al. | |
| 2007/0195922 A1 | 8/2007 | Mackie et al. | |
| 2007/0195929 A1 | 8/2007 | Ruchala et al. | |
| 2007/0195930 A1 | 8/2007 | Kapatoes et al. | |
| 2007/0197908 A1 | 8/2007 | Ruchala et al. | |
| 2007/0201613 A1 | 8/2007 | Lu et al. | |
| 2007/0211857 A1 | 9/2007 | Urano et al. | |
| 2007/0230654 A1 | 10/2007 | Chappo et al. | |
| 2007/0238957 A1 | 10/2007 | Yared | |
| 2008/0002809 A1 | 1/2008 | Bodduluri | |
| 2008/0002811 A1 | 1/2008 | Allison | |
| 2008/0008291 A1 | 1/2008 | Alakuijala et al. | |
| 2008/0031406 A1 | 2/2008 | Yan et al. | |
| 2008/0049896 A1 | 2/2008 | Kuduvalli | |
| 2008/0064953 A1 | 3/2008 | Falco | |
| 2008/0279328 A1 | 11/2008 | Zeitler et al. | |
| 2009/0041200 A1* | 2/2009 | Lu et al. | 378/152 |
| 2009/0116616 A1 | 5/2009 | Lu et al. | |
| 2009/0252291 A1 | 10/2009 | Lu et al. | |
| 2010/0053208 A1 | 3/2010 | Menningen et al. | |
| 2010/0054413 A1 | 3/2010 | Sobering et al. | |
| 2011/0019889 A1 | 1/2011 | Gering et al. | |
| 2011/0107515 A1 | 5/2011 | Brunker et al. | |
| 2011/0112351 A1 | 5/2011 | Fordyce et al. | |

FOREIGN PATENT DOCUMENTS

| | | |
|---|---|---|
| EP | 1419801 | 3/2010 |
| JP | 63209667 | 8/1988 |
| JP | 1209077 | 8/1989 |
| JP | 6007464 | 1/1994 |
| JP | 10052421 | 2/1998 |
| JP | 10501151 | 2/1998 |
| JP | 11244401 | 9/1999 |
| JP | 2001340474 | 12/2001 |
| JP | 2002186678 | 7/2002 |
| JP | 2002210029 | 7/2002 |
| JP | 2002522128 | 7/2002 |
| JP | 2002522129 | 7/2002 |
| JP | 2003250917 | 9/2003 |
| JP | 2004166975 | 6/2004 |
| JP | 2004275636 | 10/2004 |
| JP | 2004321502 | 11/2004 |
| JP | 2005160804 | 6/2005 |
| JP | 2005518908 | 6/2005 |
| JP | 2007509644 | 4/2007 |
| JP | 2007516743 | 6/2007 |
| TW | 300853 | 3/1997 |
| WO | 9202277 | 2/1992 |
| WO | 0007669 | 2/2000 |
| WO | 03032838 | 4/2003 |
| WO | 03076003 | 9/2003 |
| WO | 03092789 | 11/2003 |
| WO | 03099380 | 12/2003 |
| WO | 2004057515 | 7/2004 |
| WO | 2004064641 | 8/2004 |
| WO | 2004080522 | 9/2004 |
| WO | 2004105574 | 12/2004 |
| WO | 2005035061 | 4/2005 |
| WO | 2005057463 | 6/2005 |
| WO | 2007079854 | 7/2007 |

OTHER PUBLICATIONS

PCT/US06/28533 International Search Report and Written Opinion mailed Sep. 11, 2007.

Ronald D. Rogus et al., "Accuracy of a Photogrammetry-Based Patient Positioning and Monitoring System for Radiation Therapy," Medical Physics, vol. 26, Issue 5, May 1999.

D. Rueckert et al, "Nonrigid Registration Using Free-Form Deformations: Application to Breast MR Images," IEEE Transactions on Medical Imaging, vol. 18, No. 8, Aug. 1999.

Yuan-Nan Young, "Registraion-Based Morphing of Active Contours for Segmentation of CT Scans," Mathematical Biosciences and Engineering, vol. 2, No. 1, Jan. 2005.

Anthony Yezzi et al., "A Variational Framework for Joint Segmentation and Registration," Mathematical Method in Biomedical Image Analysis, 2001. (Note: the title of the periodical and the date

(56) References Cited

OTHER PUBLICATIONS listed are from the International Search Report, however they do not appear on the article itself.).
Ruchala, Kenneth, et al., "Adaptive IMRT with Tomotherapy", RT Image, vol. 14, No. 25, pp. 14-18, Jun. 18, 2001.
Marcelo Bertalmio, et al., "Morphing Active Contours", IEEE Translations on Pattern Analysis and Machine Intelligence, vol. 22, No. 7, pp. 733-737, Jul. 2000.
Lu, W., et al., "Automatic Re-Contouring 4D Radiotherapy", Physical Medical Biology, 2006, Mar. 7, 51 (5): 1077-99.
Lu, W., et al., 2004 Automatic Re-Contouring for 4-D Planning and Adaptive Radiotherapy, The 90th RSNA Meeting, Chicago, Illinois, (abstract: Radiology 227 p. 543).
Lu, W., et al., 2004 Automatic Re-Contouring Regions of Interest Based on Deformable Registration and Surface Construction, AAPM 2004, (abstract: Medical Physics 31, 1845-6).
Purdy, James, "3D Treatment Planning and Intensity-Modulated Radiation Therapy," Oncology, vol. 13, No. 10, suppl. 5 (Oct. 1999).
Yu, Cedric X., et al., "A Method for Implementing Dynamic Photon Beam Intensity Modulation using Independent Jaws and a Multileaf Collimator," Phys. Med. Biol. 40. 1995: 769-787.
Lee, Jason et al., "Intensity Modulated Radiation Therapy; An Introduction for Patients and Clinicians," www.oncolink.com/templates/treatment/article.cfm?c=45&s=33&id=182; Jun. 16, 2001.
Keall, Paul, "4-Dimensional Computed Tomography Imaging and Treatment Planning," Seminars in Radiation Oncology, vol. 14, No. 1, Jan. 2004; pp. 81-90.
Kudo et al., "Helical-scan Computed Tomography Using Cone-Beam Projections," IEEE Conference 1991, ISBN: 0-7803-0513, vol. 3, pp. 1958-1962.
Lof, J. et al., "An Adaptive Control Algorithm for Optimization of Intensity Modulated Radiotherapy Considering Uncertainties in Beam Profiles, Patient Set-Up and Internal Organ Motion", Physics in Medicine and Biology 43, 1605-1628, Printed in the UK, 1998.
Mackie, T. Rockwell et al., "Tomotherapy" Seminars in Radiation Oncology, vol. 9, No. 1, Jan. 1, 1999, pp. 108-117, XP002603992.
Miller, Karen, "The Phantom Torso", RT Image, vol. 14 No. 25, Jun. 18, 2001.
Olivera, G. et al. "Dynamic Tangents and Topotherapy: New Delivery Capabilities for Helical Tomotherapy" Medical Physics [Online],vol. 32, No. 6, Jun. 1, 2005, pp. 2034-2034, XP002603991.
Michalski, Jeff M. et al., Three-Dimensional Conformal Radiation Therapy (3DCRT) for Prostate Cancer,: The Prostate Cancer InfoLink, Jul. 6, 1996.
Office Action from Chinese Patent Office for Application No. 200680034654.X dated Jul. 3, 2009.
Office Action from Chinese Patent Office for Application No. 200680034654.X dated Feb. 11, 2011.
Extended Search Report from European Patent Office for Application No. 06788221.7 dated Nov. 4, 2010.
PCT/US2009/043611 International Search Report and Written Opinion mailed Dec. 3, 2009.
English translation of the Office Action from the Japanese Patent Office for Application No. 2008-523014 dated Jan. 6, 2012 (2 pages).
Office Action from U.S. Patent and Trademark Office for U.S. Appl. No. 12/220,608 dated Dec. 8, 2010.
Mackie, T. Rockwell et al., "Tomotherapy: Rethinking the Processes of Radiotherapy," XIIth ICCR, May 27-30, 1997.
Fang, Guang Y. et al., "Software system for the UW/GE tomotherapy prototype," Xiith ICCR, May 27-30, 1997.
Rietzel, Eike et al., "Four-Dimensional Image-Based Treatment Planning: Target Volume Segmentation and Dose Calculation in the Presence of Respiratory Motion," International Journal of Radiation: Oncology Biology Physics, vol. 61, No. 5, pp. 1535-1550 (Apr. 1, 2005).
Office Action from Chinese Patent Office for Application No. 200680034654.X dated Mar. 26, 2012.
Office Action from U.S. Patent and Trademark Office for U.S. Appl. No. 12/220,608 dated Aug. 31, 2012.
English translation of the Office Action from the Japanese Patent Office for Application No. 2008-523014 dated Oct. 24, 2012.
Office Action from U.S. Patent and Trademark Office for U.S. Appl. No. 12/220,608 dated Apr. 25, 2013.
Office Action from European Patent Office for Application No. 06788221.7 dated Oct. 21, 2013.
Office Action from U.S. Patent and Trademark Office for U.S. Appl. No. 12/220,608 dated Mar. 28, 2014.
Office Action from European Patent Office for Application No. 06788221.7 dated Jun. 11, 2015.

\* cited by examiner

RADIATION THERAPY IMAGING AND DELIVERY UTILIZING COORDINATED MOTION OF GANTRY AND COUCH

RELATED APPLICATIONS

This application claims priority to U.S. Provisional Patent Application No. 60/701,585, filed on Jul. 23, 2005, titled RADIATION THERAPY IMAGING AND DELIVERY UTILIZING COORDINATED MOTION OF GANTRY, COUCH AND MULTI-LEAF COLLIMATOR, the entire contents of which are incorporated herein by reference.

BACKGROUND

In traditional radiation therapy, a patient lies atop a static treatment couch, and is treated by a static treatment gantry. Often, static blocks are inserted into a beam of radiation to shape the beam. As radiation therapy has advanced, motion has been introduced to improve the quality of treatment and deliver treatments more efficiently.

SUMMARY

One method in the field of radiation therapy entails simultaneous motion of multi-leaf collimator ("MLC") leaves while the patient couch and the gantry, holding the radiation source, remain still. This is referred to as dynamic MLC or a sliding-window technique and can improve delivery efficiency of a series of fixed MLC patterns. Another method is to rotate the gantry in arcs concurrently with MLC motion. This is referred to as intensity modulated arc therapy ("IMAT"). Axial radiation therapy combines MLC motion with gantry rotation and couch movement between rotations. A more advanced version, known as helical radiation therapy, entails simultaneous couch motion concurrently with MLC motion and gantry rotation. The combination of gantry rotation and patient translation results in the radiation source following a helical trajectory about the patient.

In one embodiment, the invention provides methods of performing both patient imaging and radiation therapy treatment through new and advanced motion trajectories of the radiation therapy components. These methods include novel ways of delivering treatment and producing imaging using simultaneous couch, MLC motion, and gantry rotation.

One embodiment of the invention includes a method of delivering a radiation therapy treatment plan to a patient using a radiation therapy system including a moveable support for supporting a patient and a non-ring-shaped gantry moveable relative to the support and supporting a radiation source and a multi-leaf collimator for modulating the radiation during delivery of the treatment plan. The method includes the acts of moving the support along an axis during delivery of the treatment plan, and maintaining the non-ring-shaped gantry at a fixed angle relative to the support during delivery of the treatment plan.

In another embodiment, the invention includes a method of delivering a radiation therapy treatment plan to a patient using a radiation therapy system including a moveable support for supporting a patient and a non-ring-shaped gantry moveable relative to the support and supporting a radiation source and a multi-leaf collimator for modulating the radiation during delivery of the treatment plan. The method includes the acts of moving the support along an axis during delivery of the treatment plan, and moving the non-ring-shaped gantry relative to the support during delivery of the treatment plan.

In another embodiment, the invention includes a method of delivering a radiation therapy treatment plan to a patient using a radiation therapy system including a radiation source and a moveable support for supporting a patient. The method includes the acts of moving the support along an axis, moving the radiation source in a non-circular path relative to the support, and dynamically changing one of a speed and a direction of one of the support and the radiation source during delivery of the treatment plan.

In yet another embodiment, the invention includes a method of delivering a radiation therapy treatment plan to a patient using a radiation therapy system including a radiation source and a moveable support for supporting a patient. The method includes the acts of moving the support along an axis during delivery of the treatment plan, and maintaining the radiation source at a fixed angle relative to the support during delivery of the treatment plan.

In another embodiment, the invention includes a method of delivering a radiation therapy treatment plan to a patient using a radiation therapy system including a moveable support for supporting a patient and a non-ring-shaped gantry moveable relative to the support and supporting a radiation source and a multi-leaf collimator for modulating the radiation during delivery of the treatment plan. The method includes the acts of moving the support along an axis during delivery of the treatment plan, moving the non-ring-shaped gantry relative to the support during delivery of the treatment plan, and acquiring image data of at least a portion of the patient with a radiation beam having a cone-beam geometry.

Other aspects of the invention will become apparent by consideration of the detailed description and accompanying drawings.

DETAILED DESCRIPTION

Figure 1:
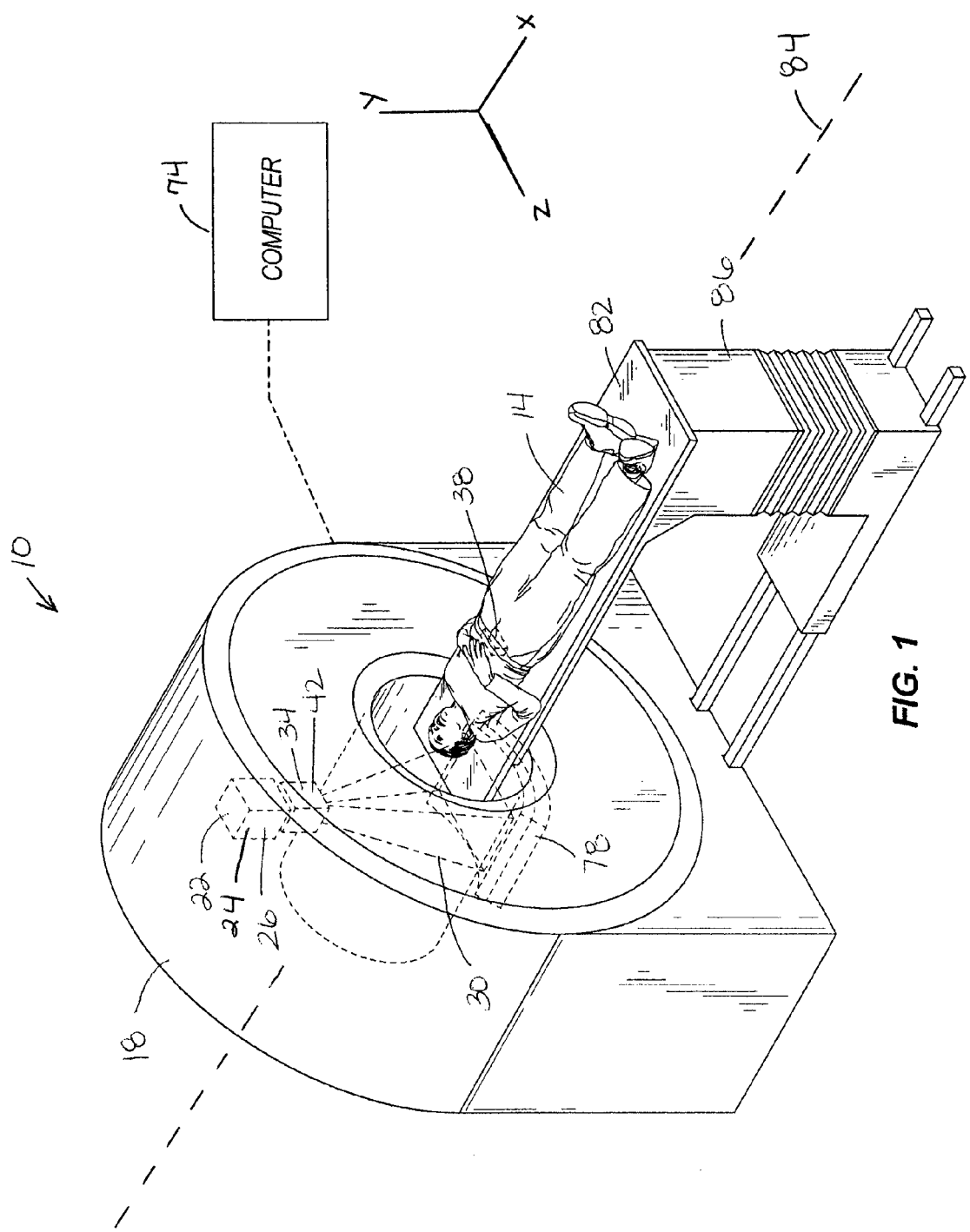
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first", "second", and "third" are used herein for purposes of description and are not intended to indicate or imply relative importance or significance.

In addition, it should be understood that embodiments of the invention include both hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software. As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 that can provide radiation therapy to a patient 14. The radiation therapy treatment can include photon-based radiation therapy, brachytherapy, electron beam therapy, proton, neutron, or particle therapy, or other types of treatment therapy. The radiation therapy treatment system 10 includes a gantry 18. The gantry 18 can support a radiation module 22, which can include a radiation source 24 and a linear accelerator 26 operable to generate a beam 30 of radiation. Though the gantry 18 shown in the drawings is a ring gantry, i.e., it extends through a full 360° arc to create a complete ring or circle, other types of mounting arrangements may also be employed. For example, a non-ring-shaped gantry, such as a C-type, partial ring gantry, or robotic arm could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped.

The radiation module 22 can also include a modulation device 34 operable to modify or modulate the radiation beam 30. The modulation device 34 provides the modulation of the radiation beam 30 and directs the radiation beam 30 toward the patient 14. Specifically, the radiation beam 34 is directed toward a portion of the patient. Broadly speaking, the portion may include the entire body, but is generally smaller than the entire body and can be defined by a two-dimensional area and/or a three-dimensional volume. A portion desired to receive the radiation, which may be referred to as a target 38 or target region, is an example of a region of interest. Another type of region of interest is a region at risk. If a portion includes a region at risk, the radiation beam is preferably diverted from the region at risk. The patient 14 may have more than one target region that needs to receive radiation therapy. Such modulation is sometimes referred to as intensity modulated radiation therapy ("IMRT").

Figure 2:
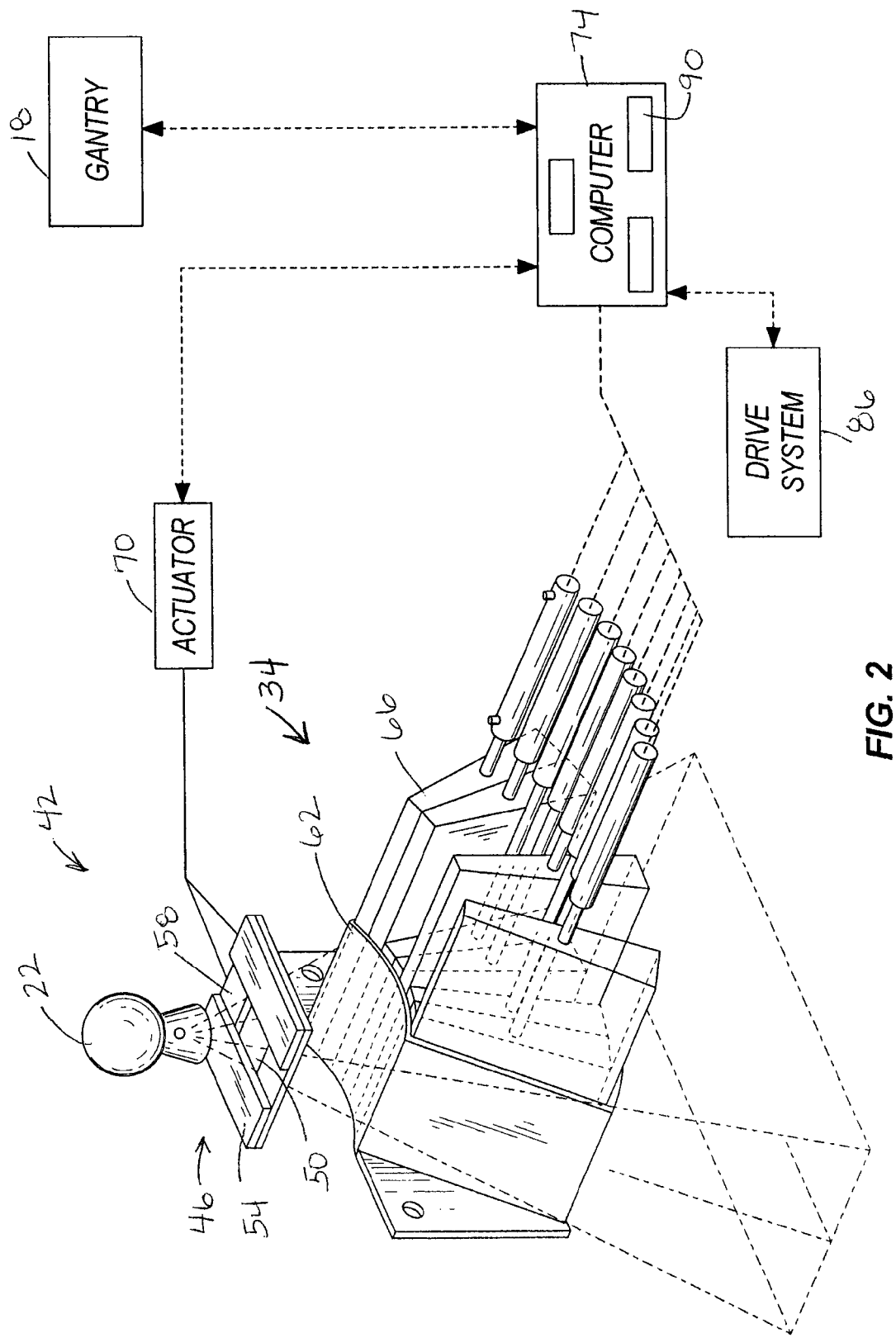
FIG. 2 is a perspective view of a multi-leaf collimator that can be used in the radiation therapy treatment system illustrated in FIG. 1.

The modulation device 34 can include a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50.

In one embodiment, and illustrated in FIG. 2, the modulation device 34 can comprise a multi-leaf collimator 62, which includes a plurality of interlaced leaves 66 operable to move from position to position, to provide intensity modulation. It is also noted that the leaves 66 can be moved to a position anywhere between a minimally and maximally-open position. The plurality of interlaced leaves 66 modulate the strength, size, and shape of the radiation beam 30 before the radiation beam 30 reaches the target 38 on the patient 14. Each of the leaves 66 is independently controlled by an actuator 70, such as a motor or an air valve so that the leaf 66 can open and close quickly to permit or block the passage of radiation. The actuators 70 can be controlled by a computer 74 and/or controller.

The radiation therapy treatment system 10 can also include a detector 78, e.g., a kilovoltage or a megavoltage detector, operable to receive the radiation beam 30. The linear accelerator 26 and the detector 78 can also operate as a computed tomography (CT) system to generate CT images of the patient 14. The linear accelerator 26 emits the radiation beam 30 toward the target 38 in the patient 14. The target 38 absorbs some of the radiation. The detector 78 detects or measures the amount of radiation absorbed by the target 38. The detector 78 collects the absorption data from different angles as the linear accelerator 26 rotates around and emits radiation toward the patient 14. The collected absorption data is transmitted to the computer 74 to process the absorption data and to generate images of the patient's body tissues and organs. The images can also illustrate bone, soft tissues, and blood vessels.

The CT images can be acquired with a radiation beam 30 that has a fan-shaped geometry, a multi-slice geometry or a cone-beam geometry. In addition, the CT images can be acquired with the linear accelerator 26 delivering megavoltage energies or kilovoltage energies. It is also noted that the acquired CT images can be registered with previously acquired CT images (from the radiation therapy treatment system 10 or other image acquisition devices, such as other CT scanners, MRI systems, and PET systems). For example, the previously acquired CT images for the patient 14 can include identified targets 38 made through a contouring process. The newly acquired CT images for the patient 14 can be registered with the previously acquired CT images to assist in identifying the targets 38 in the new CT images. The registration process can use rigid or deformable registration tools.

In some embodiments, the radiation therapy treatment system 10 can include an x-ray source and a CT image detector. The x-ray source and the CT image detector operate in a similar manner as the linear accelerator 26 and the detector 78 as described above to acquire image data. The image data is transmitted to the computer 74 where it is processed to generate images of the patient's body tissues and organs.

The radiation therapy treatment system 10 can also include a patient support, such as a couch 82 (illustrated in FIG. 1), which supports the patient 14. The couch 82 moves along at least one axis 84 in the x, y, or z directions. In other embodiments of the invention, the patient support can be a device that is adapted to support any portion of the patient's body. The patient support is not limited to having to support the entire patient's body. The system 10 also can include a drive system 86 operable to manipulate the position of the couch 82. The drive system 86 can be controlled by the computer 74.

Figure 3:
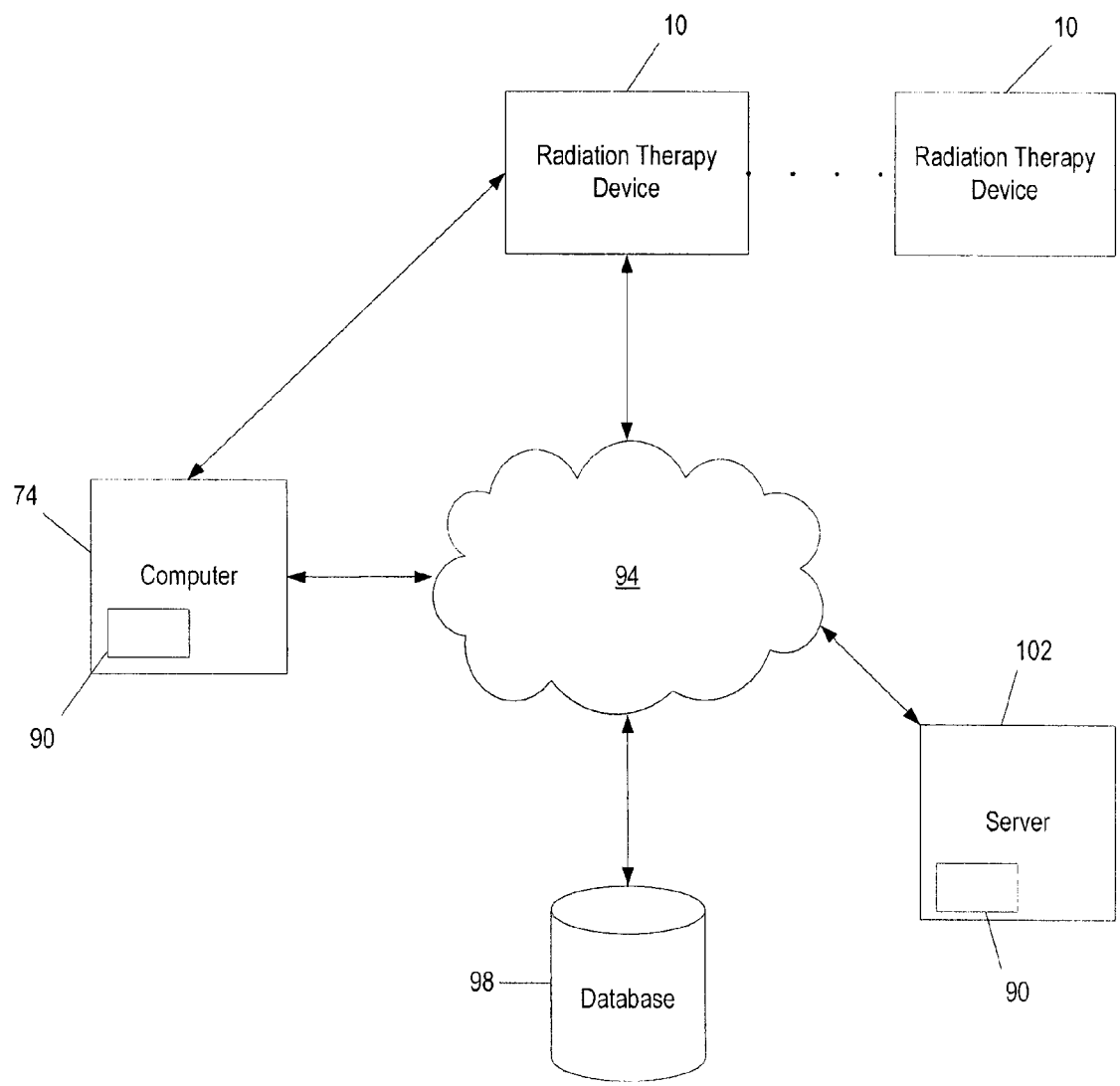
FIG. 3 is a schematic illustration of the radiation therapy treatment system of FIG. 1.

The computer 74, illustrated in FIGS. 2 and 3, includes an operating system for running various software programs and/or a communications application. In particular, the computer 74 can include a software program(s) 90 that operates to communicate with the radiation therapy treatment system 10. The computer 74 can include any suitable input/output device adapted to be accessed by medical personnel. The computer 74 can include typical hardware such as a processor, I/O interfaces, and storage devices or memory. The computer 74 can also include input devices such as a keyboard and a mouse. The computer 74 can further include standard output devices, such as a monitor. In addition, the computer 74 can include peripherals, such as a printer and a scanner.

The computer 74 can be networked with other computers 74 and radiation therapy treatment systems 10. The other computers 74 may include additional and/or different computer programs and software and are not required to be identical to the computer 74, described herein. The computers 74 and radiation therapy treatment system 10 can communicate with a network 94. The computers 74 and radiation therapy treatment systems 10 can also communicate with a database(s) 98 and a server(s) 102. It is noted that the software program(s) 90 could also reside on the server(s) 102.

The network 94 can be built according to any networking technology or topology or combinations of technologies and topologies and can include multiple sub-networks. Connections between the computers and systems shown in FIG. 3 can be made through local area networks ("LANs"), wide area networks ("WANs"), public switched telephone networks ("PSTNs"), wireless networks, Intranets, the Internet, or any other suitable networks. In a hospital or medical care facility, communication between the computers and systems shown in FIG. 3 can be made through the Health Level Seven ("HL7") protocol or other protocols with any version and/or other required protocol. HL7 is a standard protocol which specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers and systems shown in FIG. 3 can also occur through the Digital Imaging and Communications in Medicine (DICOM) protocol with any version and/or other required protocol. DICOM is an international communications standard developed by NEMA that defines the format used to transfer medical image-related data between different pieces of medical equipment. DICOM RT refers to the standards that are specific to radiation therapy data.

The two-way arrows in FIG. 3 generally represent two-way communication and information transfer between the network 94 and any one of the computers 74 and the systems 10 shown in FIG. 3. However, for some medical and computerized equipment, only one-way communication and information transfer may be necessary.

Figure 4:
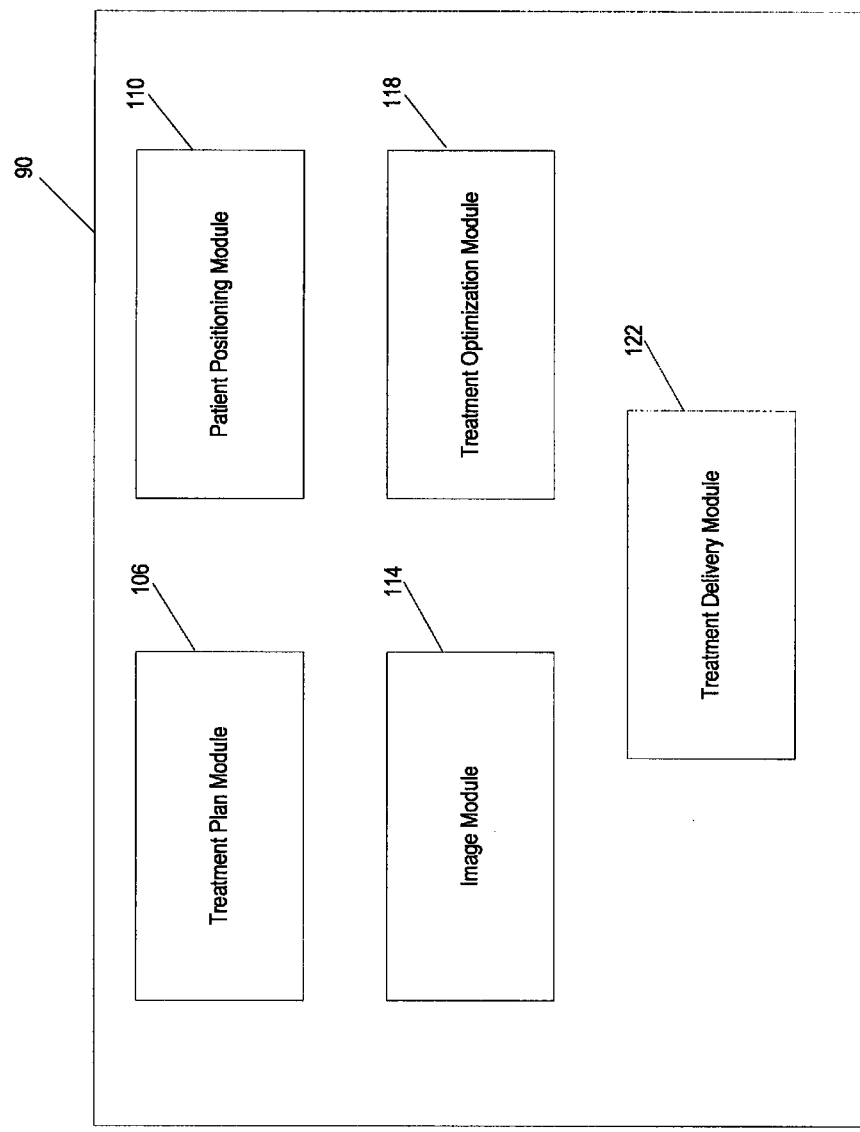
FIG. 4 is a schematic diagram of a software program used in the radiation therapy treatment system.

FIG. 4 is a schematic illustration of the software program 90. The software program 90 includes a plurality of modules that communicate with one another to perform functions of the radiation therapy treatment process. The various modules are adapted to communicate with one another to deliver radiation therapy to the patient 14.

The software program 90 includes a treatment plan module 106 operable to generate a treatment plan for the patient 14 based on data input to the system 10 by medical personnel. The data includes one or more images (e.g., planning images and/or pre-treatment images) of at least a portion of the patient 14. The treatment plan module 106 separates the treatment into a plurality of fractions and determines the radiation dose for each fraction or treatment based on the prescription input by medical personnel. The treatment plan module 106 also determines the radiation dose for the target 38 based on various contours drawn around the target 38. Multiple targets 38 may be present and included in the same treatment plan.

The software program 90 also includes a patient positioning module 110 operable to position and align the patient 14 with respect to the isocenter of the gantry 18 or other reference for a particular treatment fraction. While the patient 14 is on the couch 82, the patient positioning module 110 acquires an image of the patient 14 and compares the current position of the patient 14 to the position of the patient in a planning or previously acquired image. If the patient's position needs to be adjusted, the patient positioning module 110 provides instructions to the drive system 86 to move the couch 82, or the patient 14 can be manually moved to a new position.

In one aspect, the patient positioning module 110 can receive data from lasers positioned in the treatment room to provide patient position data with respect to the isocenter of the gantry 18 or other reference. Based on the data from the lasers, the patient positioning module 110 provides instructions to the drive system 86, which moves the couch 82 to achieve proper alignment of the patient 14 with respect to the gantry 18 or other reference. It is noted that devices and systems, other than lasers, can be used to provide data to the patient positioning module 110 to assist in the alignment process.

The software program 90 also includes an image module 114 operable to acquire images of at least a portion of the patient 14. The image module 114 can instruct the on-board image device, such as a CT imaging device to acquire images of the patient 14 before treatment commences, during treatment, and after treatment according to desired protocols. In one aspect, the image module 114 acquires an image of the patient 14 while the patient 14 is substantially in a treatment position. Other imaging devices may be used to acquire pre-treatment images of the patient 14, such as non-quantitative CT, MRI, PET, SPECT, ultrasound, transmission imaging, fluoroscopy, RF-based localization, and the like. The acquired images can be used for registration of the patient 14.

The software program 90 can include a treatment optimization module 118 operable to optimize the treatment plan generated by the treatment plan module 106. In particular, the optimization module 118 generates the commands or instructions for the radiation therapy treatment system 10 necessary to optimally deliver the treatment plan. The optimization module 118 is operable to determine and select between various parameters of operation of the radiation therapy treatment system 10 based on the type of treatment the patient 14 is going to receive and/or the mode of operation of the radiation therapy treatment system 10. Some of the parameters include, but are not limited to, position of the leaves 66, gantry angles and angular speed, speed of the drive system 86, type of motion of the couch 82, size of the jaw aperture 50, couch range of motion, and radiation beam intensity.

The optimization module 118 allows a technician or health care professional to select a mode of operation for the radiation therapy treatment system 10 and related devices assisting in radiation therapy. The modes of operation can include a manual mode, a semi-automatic mode, an automatic mode, or a combination of these modes. Alternatively, the software program 90 and/or the optimization module 118 can include sub-modules operable to selectively adjust parameters of the radiation therapy treatment system 10 pertaining to specific stages of radiation treatment.

The optimization module 118 communicates with the treatment plan module 106 to determine the settings for the radiation therapy treatment system 10 based on the type of treatment that is to be delivered as set forth in the treatment plan. In one type of treatment plan delivery, the radiation therapy treatment system 10 can be configured to position the patient 14 on the couch 82 and deliver radiation to the patient 14 by moving the couch 82, at least partially, through the gantry opening at least on one occasion while the gantry 18 is maintained at a set position or angle. This is sometimes referred to as topotherapy. It is noted that the entire length of the patient 14 does not need to pass through the gantry opening, but rather, any portion of the patient can pass or lie within the gantry opening. It is also noted that the couch 82 can move in a step-wise fashion, in a constant linear motion, and/or a combination of both types of motion. In this aspect, the desired gantry angle(s) can be selected for one or more, at least partial, passes of the patient 14 through the gantry opening. The health care professional can also specify other parameters of the radiation therapy treatment system 10. In some aspects, the optimization module 118 can automatically set the parameters of the radiation treatment therapy system 10 for each pass of the patient 14 through the gantry 18 opening. The parameters automatically set by the optimization module 118 can include, but are not limited to, number of passes of the patient 14 through the gantry 18 opening, gantry angle(s), speed of the drive system, couch range of motion, size of the jaw aperture 45, and radiation beam intensity.

The optimization module 118 can also provide instructions to the image module 114 to perform topographic and/or tomographic imaging of the patient 14 using the radiation therapy treatment system 10. The optimization module 118 can select various settings for topographic and/or tomographic imaging including the number of passes that the patient 14 travels through the gantry opening, gantry angles, speed of the drive system 86, couch range of motion, size of the jaws aperture 50, and radiation beam intensity.

The optimization module 118 can include a scan-plan-treat mode. The scan-plan-treat mode includes a sequence of scanning the patient 14, generating a treatment plan, and treating the patient 14 in one session using the radiation therapy treatment system 10 without interruption. The radiation therapy treatment system 10 integrates positioning of the patient 14, treatment planning, and delivery of the plan in a single system. There is less need to transport the patient 14 to numerous departments in a medical facility for radiation therapy. As a result of the system integration and use of geometric shapes to identify contours in some circumstances, a patient 14 can be treated in approximately 20 minutes or less. For example, it should take about two minutes to position the patient 14 on the couch 82, about three to about six minutes to acquire the CT images, about three minutes to identify the contours, about two minutes to generate the treatment plan, and about three minutes to deliver the plan.

In some aspects, the optimization module 118 provides optimization methods for one or more topographic passes. These can be manually implemented by the user, or automatically implemented by the system 10. These methods include identifying and/or optimizing preferred gantry angles, pitches, gantry speeds, jaw aperture, couch speed, and/or couch range of motion.

Another embodiment of the invention includes extending the target 38 to include a wider area. This process is sometimes referred to as leaf flashing and involves increasing the area of the radiation beam 30 in response to motion of the patient 14 during treatment. For example, some organs of the patient 14 may expand and contract as the patient 14 receives radiation therapy treatment. The leaf flashing process can utilize pre-treatment and/or during-treatment images to determine the additional margin(s) around the target 38 that may need treatment. For example, a pre-determined target 38 located at the breast area of a patient 14 can be treated with the leaf flashing procedure. The breast area can contract and expand as the patient 14 breathes. The leaf flashing procedure allows a health care professional to observe changes of the breast area in the form of images and to adjust the radiation treatment to cover the margin(s) of the target 38 during at least a fraction of the overall treatment. Alternatively, the optimization module 118 can include instructions for the radiation therapy treatment system 10 to automatically perform the leaf flashing procedure by obtaining images and adjusting the treatment based on the images and expected changes in the anatomy of the patient 14. The computer 74 running the optimization module 118 may also perform topotherapy treatment and tomographic imaging automatically or under the supervision of a qualified user.

In another type of treatment plan delivery, the radiation therapy treatment system 10 can be configured to position the patient 14 on the couch 82 and deliver radiation to the patient 14 by moving the couch 82, at least partially, through the gantry opening at least on one occasion while the gantry 18 is rotated along a defined path. The defined path of gantry rotation is in a short arc or between a first position and a second position, where the second position is different than the first position. The defined path is less than a complete circle. This type of gantry movement combined with movement of the couch 82 is sometimes referred to as dynamic tangent.

The patient 14 undergoes an imaging procedure to obtain images that assist in identifying the target(s) 38. Based on the image(s) and/or treatment plan, the optimization module 118 can identify a start angle and an end angle for the defined path of travel of the gantry 18. The optimization module 118 can determine other parameters of the radiation therapy treatment system 10 such as range of motion of the couch 82, helix spacing, size of the jaw aperture 50, and speed of the drive system 86. The optimization module 118 provides instructions to the radiation therapy treatment system 10 to rotate the gantry 18 from the first or start position to the second or end position and to project the radiation beam 30 toward the target 38 while the couch 82 moves the patient 14 into and through the gantry opening.

The dynamic tangent procedure can also be performed as the patient 14 is moved out of the gantry opening. For example, as the patient 14 is moving through and out of the gantry opening the gantry 18 can rotate from the second or end position to the first or start position. A health care professional can view and adjust the operational parameters such as start position, end position, speed of the drive system 86, and couch range of motion for each pass through the gantry opening.

The radiation therapy treatment system 10 can deliver the treatment plan using helices of either common or opposite chirality (i.e., the direction of rotation of the helix relative to its axis), or multiples of both. Opposite chirality is achieved by reversing either the direction of movement of the couch or direction of gantry rotation for a delivery pass after a previous delivery pass.

In various aspects of the invention, treatment options can include changing gantry speeds and/or directions during imaging or treatment; changing couch speeds and/or directions during treatment; completing entire treatment passes before switching direction of the gantry; changing direction of the gantry to deliver higher or lower doses of radiation to the patient; changing direction of the gantry to correct for errors or patient motion; and/or using predictive gating to anticipate errors or patient motion and compensate for any lags in the detection/correction process. Additionally, any of the aforementioned embodiments of the dynamic tangent technique can be combined with simultaneous discrete or continuous motion of the couch 82, or of the patient using an external device. Such motion can be either discrete or continuous, and may be performed at a constant or variable rate with any combinations of translations or rotations comprising the movement.

Further embodiments include optimization of delivery through automatic detection and/or clinical observation of the patient's breathing patterns. This can include manually setting the breathing pauses, or automatically gating the linear accelerator or MLC based upon a patient movement device. In the event that the patient's breathing hinders delivery of the treatment plan, e.g., the patient's breathing becomes erratic, the procedure could continue without radiation (beam off or leaves closed) until the patient's breathing stabilizes. In this event, the system 10 can record the missed regions of the treatment. The missed regions can be cumulated into make-up procedures and run as appropriate (daily, weekly, monthly, etc.) depending on amount of radiation missed and clinical necessity.

The dynamic tangent treatment can also be combined with tomographic or topographic imaging, in which an image(s) is obtained as the patient 14 receives radiation therapy treatment. Images can be acquired by stopping or slowing the dynamic tangent procedure and employing the radiation source 24 to acquire the image or images. Once images are acquired, the dynamic tangent procedure may continue. Some alternatives include acquiring images when the gantry 18 is at the first position. Other alternatives are to acquire images at angles between the first or start position and the second or end position of the gantry 18. Based on the images obtained during treatment, a health care professional may selectively adjust the parameters of the radiation therapy treatment system 10 for subsequent passes of the patient 14, or these parameters may be adjusted automatically. Alternatively, the optimization module 118 can include instructions to automatically set dynamic tangent parameters such as the first or start position, second or end position, gantry speed, couch range of motion, speed of the drive system 86, size of the jaw aperture 50, and the position of the leaves 66.

In another type of treatment plan delivery, a back-and-forth gantry motion is combined with movement of the couch 82. In this type of treatment plan delivery, the radiation therapy treatment system 10 can be configured to position the patient 14 on the couch 82 and deliver radiation to the patient 14 by moving the couch 82, at least partially, through the gantry opening at least on one occasion while the gantry 18 rotates along a defined path in a back-and-forth motion. The defined path of gantry rotation is in a short arc or between a first position and a second position, where the second position is different than the first position. The defined path is less than a complete circle. This is sometimes referred to as rocking gantry.

The patient 14 undergoes an imaging procedure to obtain images that assist in identifying the target(s) 38. Based on the image(s) and/or treatment plan, the optimization module 118 can identify a start angle and an end angle for the defined path of travel of the gantry 18. The optimization module 118 can determine other parameters of the radiation therapy treatment system 10 such as range of motion of the couch 82, helix spacing, size of the jaw aperture 50, and speed of the drive system 86. The optimization module 118 provides instructions to the radiation therapy treatment system 10 to rotate the gantry 18 in a back-and-forth manner along the path between the first or start position to the second or end position and to project the radiation beam 30 toward the target 38 while the couch 82 moves the patient 14 into and through the gantry opening.

The rocking gantry method of treatment may also include tomographic or topographic imaging of the patient 14 in which an image(s) is obtained as the patient 14 receives radiation treatment. Images can be acquired by selectively stopping the gantry 18 at an angle between the start position and the end position, obtaining an image or images, and resuming treatment. Based on the images obtained during treatment, a health care professional can adjust the parameters of the radiation therapy treatment system 10 for subsequent passes of the patient 14.

The rocking gantry procedure can also be performed as the patient 14 is moved out of the gantry opening. For example, as the patient 14 is moving through and out of the gantry opening the gantry 18 can rotate in a back-and-forth manner from the second or end position to the first or start position. A health care professional can view and adjust the operational parameters such as start position, end position, speed of the drive system 86, and couch range of motion for each pass through the gantry opening.

Another aspect of the invention includes adjusting the radiation therapy treatment system parameters to provide therapy to the patient 14 with a plurality of identified targets 38. This is referred to as multiple region treatment and involves providing radiation treatment to a first target 38 and automatically proceeding to provide treatment to a subsequent target 38. This can provide efficient and automatic treatment to disparate targets 38. Targets 38 may require different types of treatments such as rocking gantry or dynamic tangent. The multiple region treatment procedure can incorporate various types of treatments by automatically adjusting parameters such as the size of the jaw aperture 50, position of the leaves 66, speed of the drive system 86, and couch range of motion, for each target 38 to be treated. In one pass of the patient 14 through the gantry opening, the multiple region treatment procedure can automatically adjust the position of the patient 14 between treatment sequences.

Topographic imaging may also be incorporated with the multiple region treatment procedure. Similar to other treatment procedures, CT images can be selectively acquired by stopping or slowing the radiation therapy treatment system 10 at a desired location, acquiring one or more CT images and subsequently continuing treatment. Based on the CT images obtained during treatment, a health care professional can selectively adjust treatment for each target 38 being treated. Alternatively, the optimization module 118 can include instructions to automatically determine the number of targets 38 to be treated, adjust the radiation therapy treatment system parameters for each treatment according to the characteristics of the targets 38, and reposition the patient 14 between treatments.

Another aspect of the invention includes concurrent cone beam CT ("CBCT") imaging for radiation treatments with couch motion. This process can be combined with movement of the gantry 18. This combination is referred to as helical trajectory CBCT because the radiation source 24 follows a helical path around the patient 14 as the patient 14 is moved into the gantry opening at a constant speed. Another aspect is concurrent couch motion with a static gantry 18. The radiation source 24 for CBCT imaging maintains a constant position as the patient 14 is moved by the couch 82 under the influence of the drive system 86 at a constant speed. Another aspect is concurrent couch motion with gantry rotation between a start angle and an end angle for CBCT imaging. CBCT images can be obtained while the gantry 18 rotates from the start angle to the end angle and the patient 14 is moved through the gantry opening by the couch 82. The gantry 18 can also rotate in a back-and-forth motion between the start angle and end angles as the patient 14 is moved by couch 82.

Another aspect of the invention is concurrent motion of the couch 82 with other imaging systems such as, but not limited to, PET, SPECT or MRI. Alternatively, the optimization module 118 can automatically select the operational parameters of the radiation therapy treatment system 10 for concurrent CBCT imaging, or other imaging procedures, and couch 82 motion under predetermined conditions can be selected by a health care professional.

Another aspect of the invention includes adjusting the parameters of the radiation therapy treatment system 10 to generate CT images of a plurality of the targets 38. In particular, a health care professional may adjust the parameters of the radiation therapy treatment to acquire CT images at an target 38 and proceed to a subsequent target 38 during one pass of the patient 14 through the gantry opening. Transporting the patient 14 to acquire CT images from one region to the subsequent region may require adjusting the radiation therapy treatment system parameters such as speed of the drive system 86, range of motion of the couch 82, and gantry angle. Alternatively, the optimization module 118 can automatically set the appropriate parameters for obtaining CT images in a region of interest, repositioning the patient 14, and setting appropriate parameters for CT imaging in subsequent region or regions.

The software program 90 also includes a treatment delivery module 122 operable to instruct the radiation therapy treatment system 10 to deliver the treatment plan to the patient 14 according to the treatment plan. The treatment delivery module 122 calculates the appropriate pattern, position, and intensity of the radiation beam 30 to be delivered, to match the prescription as specified by the treatment plan. The pattern of the radiation beam 30 is generated by the modulation device 34, and more particularly by movement of the plurality of leaves in the multi-leaf collimator. The treatment delivery module 122 can utilize canonical, predetermined or template leaf patterns to generate the appropriate pattern for the radiation beam 30 based on the treatment parameters. The treatment delivery module 122 can also include a library of patterns for typical cases that can be accessed in which to compare the present patient data to determine the pattern for the radiation beam 30.

Figure 5:
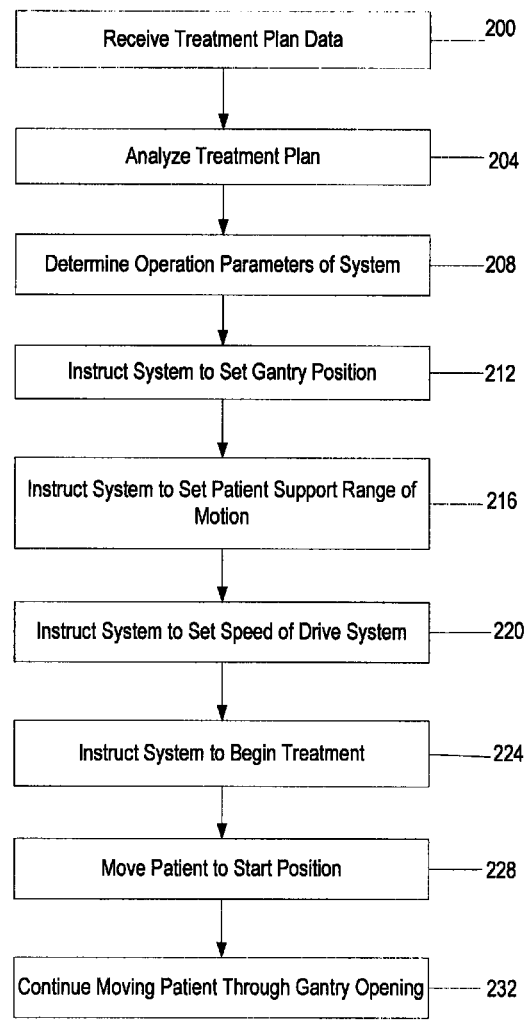
FIG. 5 is a flow chart of a method of delivering radiation therapy treatment to a patient according to one embodiment of the invention.

FIG. 5 is a flow chart of a method of treating a patient 14 with radiation therapy. Based on the treatment plan, the optimization module 118 communicates with the radiation therapy treatment system 10 to set the operational parameters. The optimization module 118 receives (at 200) the treatment plan from the treatment plan module 106. The optimization module 118 analyzes (at 204) the treatment plan and data input to the optimization module 118. Based on the treatment plan and the treatment method, the optimization module 118 determines (at 208) the operational parameters of the radiation therapy treatment system 10. The optimization module 118 instructs (at 212) the system 10 to set the position or angle of the gantry 18. The optimization module also instructs (at 216) the system 10 to set the range of motion for the couch 82 and instructs (at 220) the system 10 to set the speed of the drive system 86. After treatment begins, the speed of the drive system and direction of the couch 82 may vary from the originally set position during treatment delivery. The treatment delivery module 122 instructs (at 224) the system 10 to begin radiation therapy treatment according to the treatment plan. The drive system 86 moves (at 228) the patient 14 via the couch 82 to the start position. During treatment, the drive system 86 moves (at 232) the patient 14 via the couch 82 through the gantry opening while the gantry 18 remains in a fixed position and while the radiation source 24 delivers the radiation beam 30 to the target 38.

Figure 6:
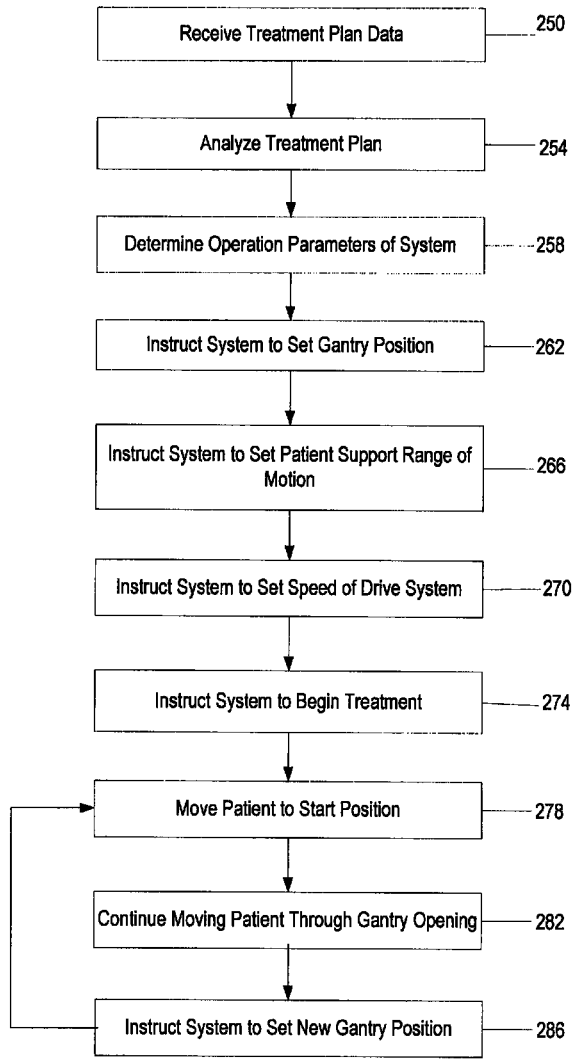
FIG. 6 is a flow chart of a method of delivering radiation therapy treatment to a patient according to one embodiment of the invention.

FIG. 6 is a flow chart of a method of treating a patient 14 with radiation therapy. The treatment plan may call for the patient 14 to travel through the gantry opening multiple times and multiple trajectories of the radiation beam. In this aspect of operation, the optimization module 118 receives (at 250) the treatment plan from the treatment plan module 106. The optimization module 118 analyzes (at 254) the treatment plan and data input to the optimization module 118. Based on the treatment plan and the treatment method, the optimization module 118 determines (at 258) the operational parameters of the radiation therapy treatment system 10. The optimization module 118 instructs (at 262) the system 10 to set the position or angle of the gantry 18. The optimization module also instructs (at 266) the system 10 to set the range of motion for the couch 82 and instructs (at 270) the system 10 to set the speed of the drive system 86. After treatment begins, the speed of the drive system and direction of the couch 82 may vary from the originally set position during treatment delivery. The treatment delivery module 122 instructs (at 274) the system 10 to begin radiation therapy treatment according to the treatment plan.

The drive system 86 moves (at 278) the patient 14 via the couch 82 to the start position.

During treatment, the drive system 86 moves (at 282) the patient 14 via the couch 82 in a first direction through the gantry opening while the gantry 18 remains in a fixed position and while the radiation source 24 delivers the radiation beam 30 to the target 38. The optimization module 118 instructs (at 286) the system 10 to set the next position or angle of the gantry 18. The range of motion of the couch 82 and the speed of the drive system 86 may also be updated or modified for the second pass through the gantry opening. Steps 278, 282, and 286 can be repeated as determined by the treatment plan. The radiation therapy treatment system 10 can store the treatment specifications, such as amount of radiation delivered to the patient 14, range of motion of the couch 82, gantry angles employed during the treatment session, and MLC parameters. The information recorded at the end of the treatment can be used to set the parameters for subsequent treatment fractions.

Figure 7:
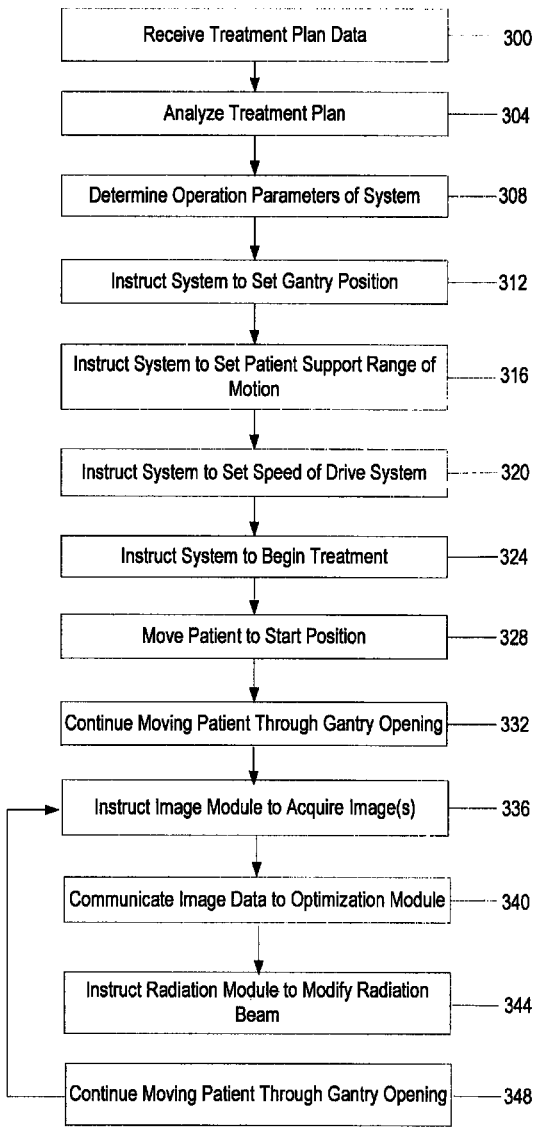
FIG. 7 is a flow chart of a method of delivering radiation therapy treatment to a patient according to one embodiment of the invention.

FIG. 7 is a flow chart of a leaf flashing method of delivering radiation treatment to a patient 14. Based on the treatment plan, the optimization module 118 communicates with the radiation therapy treatment system 10 to set the operational parameters. The optimization module 118 receives (at 300) the treatment plan from the treatment plan module 106. The optimization module 118 analyzes (at 304) the treatment plan and data input to the optimization module 118. Based on the treatment plan and the treatment method, the optimization module 118 determines (at 308) the operational parameters of the radiation therapy treatment system 10. The optimization module 118 instructs (at 312) the system 10 to set the position or angle of the gantry 18. The optimization module also instructs (at 316) the system 10 to set the range of motion for the couch 82 and instructs (at 320) the system 10 to set the speed of the drive system 86. After treatment begins, the speed of the drive system and direction of the couch 82 may vary from the originally set position during treatment delivery. The treatment delivery module 122 instructs (at 324) the system 10 to begin radiation therapy treatment according to the treatment plan. The drive system 86 moves (at 328) the patient 14 via the couch 82 to the start position.

During treatment, the drive system 86 moves (at 332) the patient 14 via the couch 82 through the gantry opening while the gantry 18 remains in a fixed position and while the radiation source 24 delivers the radiation beam 30 to the target 38. During treatment, and either while the couch 82 is slowed or stopped, the optimization module 118 instructs (at 336) the image module 114 to acquire an image(s) of at least a portion of the patient 14. As the patient 14 receives radiation treatment, the target 38 may change due to bodily functions of the patient 14, such as breathing. The image module 114 communicates (at 340) the acquired image data to the optimization module 118. The optimization module 118 instructs (at 344) the radiation module 22 to modify the radiation beam 30 to accommodate the changes in the target 38 based on the image data. Often, the parameters of the radiation beam 30 are adjusted to encompass a larger target 38 due to the changes in the patient's anatomy. The optimization module 118 instructs (at 348) the couch 82 to resume prescribed speed or operation. As the patient's anatomy changes throughout the treatment, steps 336, 340, 344, and 348 can be repeated according to the treatment plan.

Figure 8:
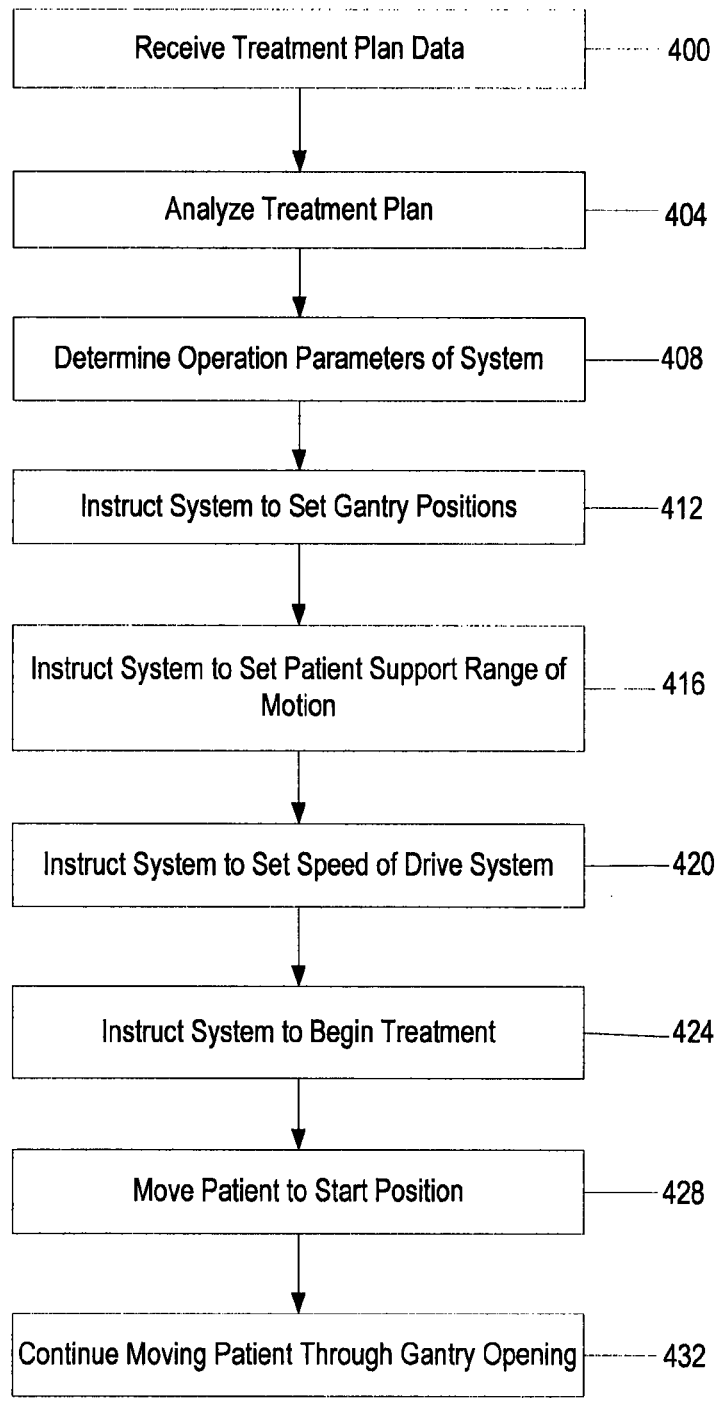
FIG. 8 is a flow chart of a method of delivering radiation therapy treatment to a patient according to one embodiment of the invention.

FIG. 8 is a flow chart of the dynamic tangent method for delivering radiation treatment. Based on the treatment plan, the optimization module 118 communicates with the radiation therapy treatment system 10 to set the operational parameters. The optimization module 118 receives (at 400) the treatment plan from the treatment plan module 106. The optimization module 118 analyzes (at 404) the treatment plan and data input to the optimization module 118. Based on the treatment plan and the treatment method, the optimization module 118 determines (at 408) the operational parameters of the radiation therapy treatment system 10. The optimization module 118 instructs (at 412) the system 10 to set the first position and second position of the gantry 18 to define a path of travel of the gantry 18. The optimization module also instructs (at 416) the system 10 to set the range of motion for the couch 82 and instructs (at 420) the system 10 to set the speed of the drive system 86. After treatment begins, the speed of the drive system and direction of the couch 82 may vary from the originally set position during treatment delivery. In one aspect, the angular speed of the gantry 18 can be determined so that the gantry 18 reaches the second position substantially at the same time as the couch 82 reaches the end position defined by the range of motion of the couch 82. The treatment delivery module 122 instructs (at 424) the system 10 to begin radiation therapy treatment according to the treatment plan. The drive system 86 moves (at 428) the patient 14 via the couch 82 to the start position. During treatment, the drive system 86 moves (at 432) the patient 14 via the couch 82 through the gantry opening while the gantry 18 rotates from the first position to the second position and while the radiation source 24 delivers the radiation beam 30 to the target 38.

As described above, while the patient 14 receives treatment, the optimization module 118 can instruct the image module 114 to acquire an image(s) of the patient 14. The image module 114 can transfer the acquired image data to the optimization module 118. The optimization module 118 can instruct the radiation module 22 to modify the radiation beam 30 to accommodate the changes in the target 38 based on the image data. Also as described above, treatment specifications can be recorded to be used in subsequent treatment fractions.

Figure 9:
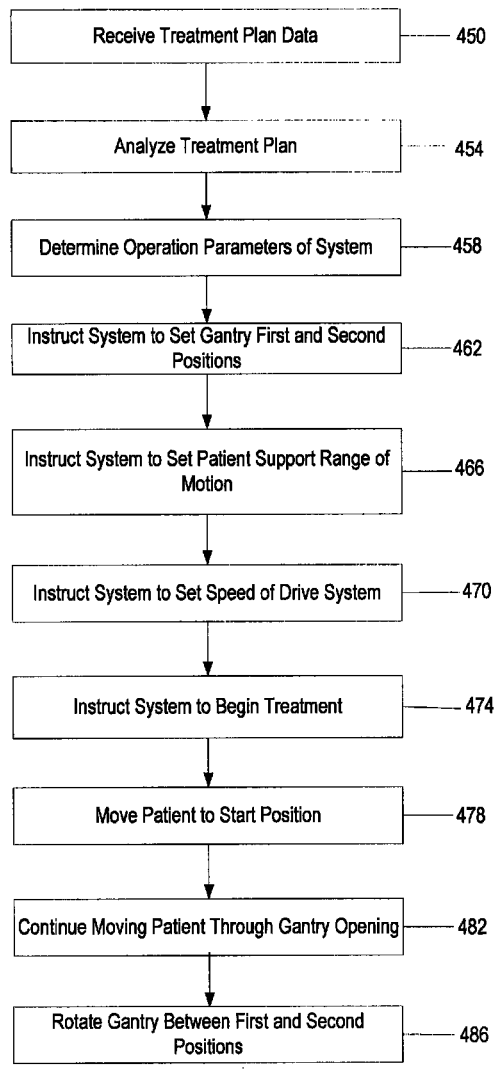
FIG. 9 is a flow chart of a method of delivering radiation therapy treatment to a patient according to one embodiment of the invention.

FIG. 9 is a flow chart of the rocking gantry method for delivering radiation treatment to a patient 14. Based on the treatment plan, the optimization module 118 communicates with the radiation therapy treatment system 10 to set the operational parameters. The optimization module 118 receives (at 450) the treatment plan from the treatment plan module 106. The optimization module 118 analyzes (at 454) the treatment plan and data input to the optimization module 118. Based on the treatment plan and the treatment method, the optimization module 118 determines (at 458) the operational parameters of the radiation therapy treatment system 10. The optimization module 118 instructs (at 462) the system 10 to set the first position and second position of the gantry 18 to define a path of travel of the gantry 18. The optimization module also instructs (at 466) the system 10 to set the range of motion for the couch 82 and instructs (at 470) the system 10 to set the speed of the drive system 86. After treatment begins, the speed of the drive system and direction of the couch 82 may vary from the originally set position during treatment delivery. The treatment delivery module 122 instructs (at 474) the system 10 to begin radiation therapy treatment according to the treatment plan. The drive system 86 moves (at 478) the patient 14 via the couch 82 to the start position. During treatment, the drive system 86 moves (at 482) the patient 14 via the couch 82 through the gantry opening while the gantry 18 rotates (at 486) between the first position and the second position and while the radiation source 24 delivers the radiation beam 30 to the target 38.

As described above, while the patient 14 receives treatment, the optimization module 118 can instruct the image module 114 to acquire an image(s) of the patient 14. The image module 114 can transfer the acquired image data to the optimization module 118. The optimization module 118 can instruct the radiation module 22 to modify the radiation beam 30 to accommodate the changes in the target 38 based on the image data. Also as described above, treatment specifications can be recorded to be used in subsequent treatment fractions.

Figure 10:
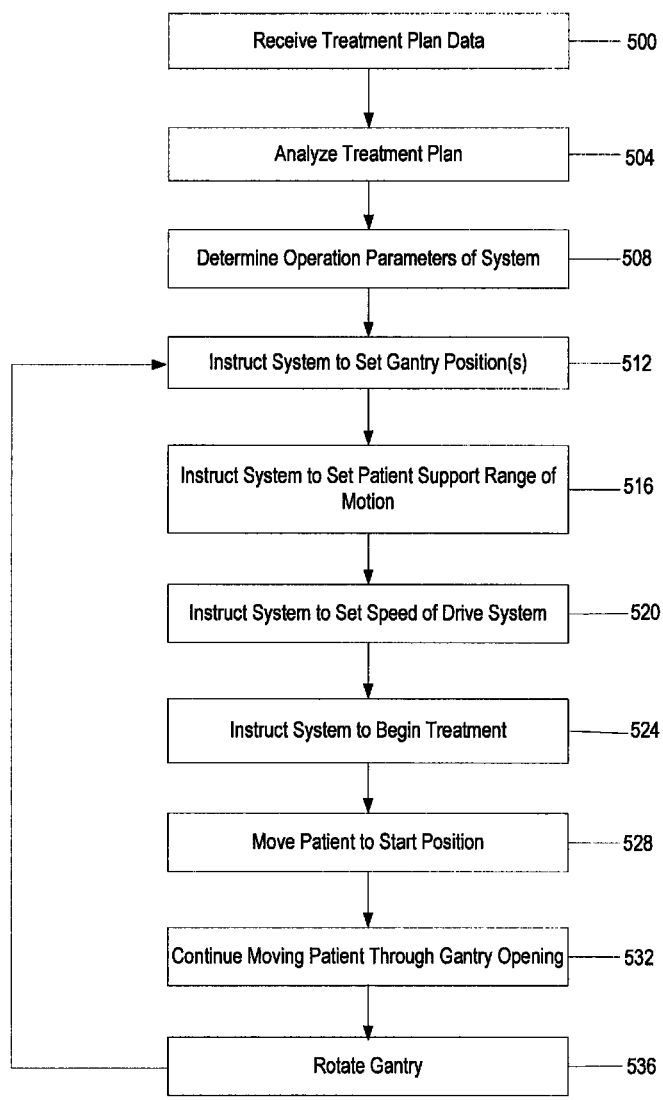
FIG. 10 is a flow chart of a method of delivering radiation therapy treatment to a patient according to one embodiment of the invention.

FIG. 10 is a flow chart of the multi-region treatment method, which may incorporate more than one radiation therapy delivery method. Based on the treatment plan, the optimization module 118 communicates with the radiation therapy treatment system 10 to set the operational parameters. The optimization module 118 receives (at 500) the treatment plan from the treatment plan module 106. The optimization module 118 analyzes (at 504) the treatment plan and data input to the optimization module 118. Based on the treatment plan and the treatment method, the optimization module 118 determines (at 508) the operational parameters of the radiation therapy treatment system 10 for each of the targets 38 to be treated. Based on the first target 38 to be treated, the optimization module 118 instructs (at 512) the system 10 to set the first position and second position of the gantry 18 to define a path of travel of the gantry 18. The optimization module also instructs (at 516) the system 10 to set the range of motion for the couch 82 and instructs (at 520) the system 10 to set the speed of the drive system 86.

After treatment begins, the speed of the drive system and direction of the couch 82 may vary from the originally set position during treatment delivery. The treatment delivery module 122 instructs (at 524) the system 10 to begin radiation therapy treatment according to the treatment plan. The drive system 86 moves (at 528) the patient 14 via the couch 82 to the start position. During treatment, the drive system 86 moves (at 532) the patient 14 via the couch 82 through the gantry opening while the gantry 18 rotates (at 536) between the first position and the second position and while the radiation source 24 delivers the radiation beam 30 to the target 38. After the first target 38 has been treated, the couch 82 can be slowed or stopped and steps 512-536 can be repeated for the second target 38. The second target 38 may receive treatment based on a different method of treatment as described above (e.g., topotherapy, dynamic tangent, rocking gantry, etc.).

As described above, while the patient 14 receives treatment, the optimization module 118 can instruct the image module 114 to acquire an image(s) of the patient 14. The image module 114 can transfer the acquired image data to the optimization module 118. The optimization module 118 can instruct the radiation module 22 to modify the radiation beam 30 to accommodate the changes in the target 38 based on the image data. Also as described above, treatment specifications can be recorded to be used in subsequent treatment fractions.

After the patient's first treatment, the same treatment plan can be used for future treatments. Subsequent fractions of the treatment plan can be modified or optimized. For example, the treatment plan can be modified to account for anatomical changes and to remedy errors in the process. In addition, subsequent fractions of the treatment plan can be modified to account for cumulative dose delivered to the target(s) 38. The fractions of the treatment plan can be modified to incorporate the effects of deformation and biological information. The fractions of the treatment plan can be additionally modified based on the initial acquired CT images or based on subsequently acquired CT images. In some embodiments, the system 10 can intersperse image acquisition phases into a radiation therapy treatment plan. This is performed by stopping the couch during a helical or topographic treatment to collect images (and simultaneously gating, stopping, or blocking radiation to the patient), imaging between passes of a multi-pass treatment, imaging between gantry angles or portals of a step-and-shoot type delivery, or imaging between arcs of an IMAT delivery. The system 10 can also provide for treatment verification through dose calculation performed concurrent with delivery of the treatment plan, through dose reconstruction incorporating detector exit data, through recalculation of dose in a 4D image based upon measurements of a patient's motion during treatment, or through modification of the treatment plan in real time or performed retrospectively based upon 4D dose calculation, and/or comparison of 4D dose calculation to the planned delivery. In the case of dose reconstruction through the use of exit data, the exit data can come from a detector such as, for example, a single-row gas ionization detector (e.g., xenon), a multi-row gas ionization detector, a crystal detector, a solid state detector, a flat panel detector (e.g., Amorphous silicon or selenium), or other suitable detecting devices.

Various features of the invention are set forth in the following claims.

What is claimed is:

1. A method of delivering a radiation therapy treatment plan to a patient using a radiation therapy system including a radiation source and a moveable support for supporting a patient, the method comprising:
   generating a radiation therapy treatment plan for the patient, the radiation therapy treatment plan including a plurality of fractions and a radiation dose for each of the plurality of fractions;
   prior to delivering one of the plurality of fractions to the patient, generating instructions, based on the radiation therapy treatment plan for implementing the radiation therapy treatment plan, for moving the support along an axis for the one of the plurality of fractions to deliver the radiation dose for the one fraction to the patient, wherein the instructions include instructions for dynamically changing a speed of the support during delivery of the one of the plurality of fractions; and
   delivering the one fraction to the patient by
   moving the support along an axis in accordance with the instructions;
   moving the radiation source relative to the support; and
   dynamically changing a speed of the support during delivery of the one fraction in accordance with the instructions.

2. A method as set forth in claim 1 wherein moving the radiation source includes moving the radiation source in a non-circular path.

3. A method as set forth in claim 2 wherein delivery of the treatment plan results in a non-helical beam trajectory.

4. A method as set forth in claim 1 and wherein moving the radiation source further comprises moving the radiation source back and forth between a first position and a second position.

5. A method as set forth in claim 4 wherein there is a pause in the delivery of radiation during the movement of the radiation source.

6. A method as set forth in claim 5 and further comprising acquiring a patient image during at least one pause.

7. A method as set forth in claim 1 wherein the radiation therapy system includes a gantry and wherein the radiation source is supported by the gantry, and further comprising setting a range of motion for the support, including a support start position and a support end position, setting a gantry start angle, and setting a gantry end angle, and coordinating the support start position with the gantry start angle and coordinating the support end position with the gantry end angle.

8. A method as set forth in claim 1 and further comprising moving the support and rotating the radiation source through multiple passes so that a radiation beam emitted from the radiation source moves through a plurality of helical pathways about the patient.

9. A method as set forth in claim 8 wherein the helical pathways share a common chirality.

10. A method as set forth in claim 8 wherein at least two of the helical pathways have opposite chirality to one another.

11. A method as set forth in claim 1 wherein the radiation therapy treatment plan defines multiple regions of interest for treatment, and further comprising coordinating motion of the support and radiation source to treat the multiple regions of interest.

12. A method as set forth in claim 11 and further comprising acquiring an image between the treatment of each region of interest, and adjusting the treatment plan based on the image.

13. A method as set forth in claim 1 and further comprising acquiring an image during movement of the support and the radiation source.

14. A method as set forth in claim 13 wherein the image is acquired using a radiation beam having a cone-beam geometry.

15. A method of delivering a radiation therapy treatment plan to a patient using a radiation therapy system including a moveable support for supporting a patient and a gantry moveable relative to the support, the method comprising:
  generating a radiation therapy treatment plan for the patient, the radiation therapy treatment plan including a plurality of fractions and a radiation dose for each of the plurality of fractions;
  prior to delivering one of the plurality of fractions to the patient, optimizing the treatment plan to generate instructions, based on the radiation therapy treatment plan for implementing the radiation therapy treatment plan, for movement of the support to deliver the radiation dose for the one of the plurality of fractions to the patient, wherein the instructions include instructions for dynamically changing a speed of the support during delivery of the one of the plurality of fractions;
  moving the support along an axis at varying speeds in accordance with the instructions during delivery of the one fraction; and
  moving the gantry relative to the support during movement of the support.

16. A method as set forth in claim 15 wherein the radiation therapy system includes a radiation source and a multi-leaf collimator, and wherein the radiation source and the multi-leaf collimator are supported by the gantry, and further comprising controlling operation of the multi-leaf collimator simultaneously with moving the support and moving the gantry.

17. A method as set forth in claim 15 and further comprising observing changes to a region of interest during delivery of radiation, and adjusting delivery during at least a fraction of the treatment plan.

18. A method as set forth in claim 17 wherein observing changes to a region of interest during delivery of radiation includes modifying the region of interest receiving radiation to account for the changes to the region of interest.

19. A method as set forth in claim 15 and further comprising moving the gantry to a different angle relative to the support during delivery of the treatment plan.

20. A method as set forth in claim 15 further comprising acquiring an image of at least a portion of the patient while the patient is in a treatment position.

21. A method of delivering a radiation therapy treatment plan to a patient using a radiation therapy system including a radiation source and a moveable support for supporting a patient, the method comprising:
  generating a radiation therapy treatment plan for the patient, the radiation therapy treatment plan including a plurality of fractions and a radiation dose for each of the plurality of fractions;
  prior to delivering one of the plurality of fractions to the patient, generating instructions, based on the radiation therapy treatment plan for implementing the radiation therapy treatment plan, for movement of the support to deliver the radiation dose for the one of the plurality of fractions to the patient, wherein the instructions include instructions for dynamically changing a speed of the support during delivery of the one of the plurality of fractions;
  acquiring an image of at least a portion of the patient while the patient is in a treatment position;
  moving the support at varying speeds along an axis during delivery of the one fraction in accordance with the instructions; and
  maintaining the radiation source at a fixed angle relative to the support during movement of the support.

22. A method as set forth in claim 21 and further comprising delivering radiation to the patient based on the acquired image.

23. A method as set forth in claim 22 and further comprising moving the radiation source to a different angle relative to the support during delivery of the radiation.

24. A method as set forth in claim 21 and further comprising delivering radiation to the patient based on the treatment plan and the acquired image.

25. A method of delivering a radiation therapy treatment plan to a patient using a radiation therapy system including a moveable support for supporting a patient and a gantry moveable relative to the support and supporting a radiation source and a multi-leaf collimator for modulating the radiation during delivery of the treatment plan, the method comprising:
  generating a radiation therapy treatment plan for the patient, the radiation therapy treatment plan including a plurality of fractions and a radiation dose for each of the plurality of fractions;
  prior to delivering one of the plurality of fractions to the patient, generating instructions, based on the radiation therapy treatment plan for implementing the radiation therapy treatment plan, for movement of the support to deliver the radiation dose for the one of the plurality of fractions to the patient, wherein the instructions include instructions for dynamically changing a speed of the support during delivery of the one of the plurality of fractions;

moving the support at varying speeds along an axis during delivery of the one fraction in accordance with the instructions;

moving the gantry relative to the support during movement of the support; and acquiring image data of at least a portion of the patient with a radiation beam.

26. A method as set forth in claim 25 wherein movement of the support is performed before delivery of the treatment plan commences.

27. A method as set forth in claim 25 wherein movement of the support is performed during delivery of the treatment plan.

28. A method as set forth in claim 25 wherein acquiring image data of at least a portion of the patient occurs while the patient is in the treatment position.

29. A method as set forth in claim 28 wherein acquiring the image data of at least a portion of the patient while the patient is in the treatment position further comprises using a radiation source distinct from the radiation source of the radiation therapy system.

30. A method as set forth in claim 25 and further comprising controlling operation of the multi-leaf collimator simultaneously with moving the support and moving the gantry.

31. A method as set forth in claim 25, and further comprising observing changes to a region of interest during delivery of radiation, and adjusting delivery during at least a fraction of the treatment plan.

32. A method as set forth in claim 31 and further comprising modifying the multi-leaf collimator pattern to encompass ranges of multi-leaf collimator motion.

33. A method as set forth in claim 25 wherein the gantry is non-ring-shaped.

34. A method of delivering a radiation therapy treatment plan to a patient using a radiation therapy system including a moveable support for supporting a patient and a gantry moveable relative to the support and supporting a radiation source and a multi-leaf collimator for modulating the radiation during delivery of the treatment plan, the method comprising:

generating a radiation therapy treatment plan for the patient, the radiation therapy treatment plan including a plurality of fractions and a radiation dose for each of the plurality of fractions;

prior to delivering one of the plurality of fractions to the patient, generating instructions, based on the radiation therapy treatment plan to implement the radiation therapy treatment plan, for movement of the support based on the radiation therapy treatment plan to deliver the radiation dose for the one of the plurality of fractions to the patient, wherein the instructions include instructions for changing a speed of the support during delivery of the one of the plurality of fractions;

moving the support at varying speeds along an axis in accordance with the instructions during delivery of the one fraction;

moving the gantry relative to the support during movement of the support; and controlling operation of the multi-leaf collimator simultaneously with moving the support and moving the gantry.

35. A method of delivering a radiation therapy treatment plan to a patient using a radiation therapy system including a radiation source and a moveable support for supporting a patient, the method comprising:

generating a radiation therapy treatment plan for the patient, the radiation therapy treatment plan including a plurality of fractions and a radiation dose for each of the plurality of fractions;

prior to delivering one of the plurality of fractions to the patient, generating instructions, based on the radiation therapy treatment plan for implementing the radiation therapy treatment plan, for movement of the support based on the radiation therapy treatment plan to deliver the radiation dose for one of the plurality of fractions to the patient, wherein the instructions include instructions for dynamically changing a speed of the support during delivery of the one of the plurality of fractions;

moving the support at varying speeds along an axis in accordance with the instructions during delivery of the one fraction;

moving the radiation source relative to the support; and dynamically changing a direction of at least one of the support and the radiation source during delivery of the treatment plan in accordance with the instructions.

* * * * *